(12) United States Patent
Zhang et al.

(10) Patent No.: US 11,737,703 B2
(45) Date of Patent: *Aug. 29, 2023

(54) VISCOELASTICITY CALCULATION SYSTEM AND VISCOELASTICITY MEASUREMENT METHOD

(71) Applicant: MAXELL, LTD., Kyoto (JP)

(72) Inventors: Yuhua Zhang, Kyoto (JP); Akihiko Kandori, Kyoto (JP); Masayoshi Ishibashi, Kyoto (JP); Shinya Kajiyama, Kyoto (JP)

(73) Assignee: MAXELL, LTD., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/538,624

(22) Filed: Nov. 30, 2021

(65) Prior Publication Data

US 2022/0160292 A1 May 26, 2022

Related U.S. Application Data

(63) Continuation of application No. 15/577,085, filed as application No. PCT/JP2016/061232 on Apr. 6, 2016, now Pat. No. 11,219,407.

(30) Foreign Application Priority Data

Jun. 5, 2015 (JP) ................................. 2015-115086

(51) Int. Cl.
*A61B 5/00* (2006.01)
*A61B 5/05* (2021.01)
*A61B 5/107* (2006.01)

(52) U.S. Cl.
CPC .............. *A61B 5/442* (2013.01); *A61B 5/445* (2013.01); *A61B 5/742* (2013.01); *A61B 5/05* (2013.01);

(Continued)

(58) Field of Classification Search
CPC ......... A61B 5/442; A61B 5/445; A61B 5/742; A61B 5/05; A61B 5/1075; A61B 5/7239;
(Continued)

(56) References Cited

U.S. PATENT DOCUMENTS

| 2009/0210158 A1 | 8/2009 | German |
| 2013/0085417 A1* | 4/2013 | Kandori ................. A61B 5/103 600/587 |
| 2013/0237766 A1* | 9/2013 | Pell ...................... A61B 5/0051 600/211 |

FOREIGN PATENT DOCUMENTS

| JP | H06-142064 A | 5/1994 |
| JP | 2004-108794 A | 4/2004 |

(Continued)

OTHER PUBLICATIONS

Chinese Office Action dated Dec. 30, 2019, for Chinese Patent Application No. 201680032388.0.

*Primary Examiner* — Nathan J Jenness
*Assistant Examiner* — Severo Antonio P Lopez
(74) *Attorney, Agent, or Firm* — Volpe Koenig

(57) ABSTRACT

An object of the present invention is to provide a technique of quantitatively measuring physical properties including both viscosity and elasticity. A viscoelasticity measurement system includes a measurement apparatus, a processor, and a display apparatus. The measurement apparatus includes a movable unit continuously pressed against a measurement object, a first sensor outputting acceleration information corresponding to an acceleration of pressing-directional movement of a contact portion of the movable unit with respect to the measurement object, and a second sensor outputting reactive force information corresponding to a reactive force applied to the contact portion of the movable unit with respect to the measurement object. The processor calculates first information on an elasticity component of the (Continued)

measurement object and second information on a viscosity component of the measurement object based on the acceleration information and the reactive force information. The display apparatus displays the first information and the second information.

16 Claims, 22 Drawing Sheets

(52) U.S. Cl.
CPC ........... *A61B 5/1075* (2013.01); *A61B 5/7239* (2013.01); *A61B 5/7246* (2013.01); *A61B 5/7257* (2013.01); *A61B 2562/0219* (2013.01)

(58) Field of Classification Search
CPC ................ A61B 5/7246; A61B 5/7257; A61B 2562/0219
See application file for complete search history.

(56) References Cited

FOREIGN PATENT DOCUMENTS

| | | |
|---|---|---|
| JP | 2009-240374 A | 10/2009 |
| JP | 2013-076658 A | 4/2013 |
| WO | 2006/106852 A1 | 10/2006 |
| WO | 2015/085240 A1 | 6/2015 |

\* cited by examiner

FIG. 12
(a) ACCELERATION WAVEFORM
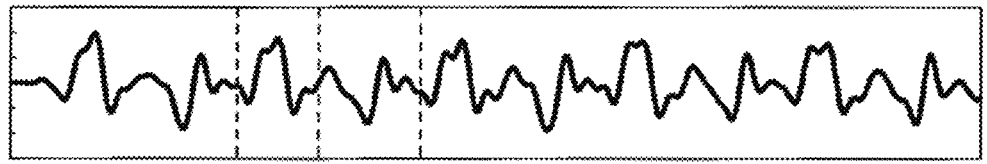
(b) VOLTAGE WAVEFORM
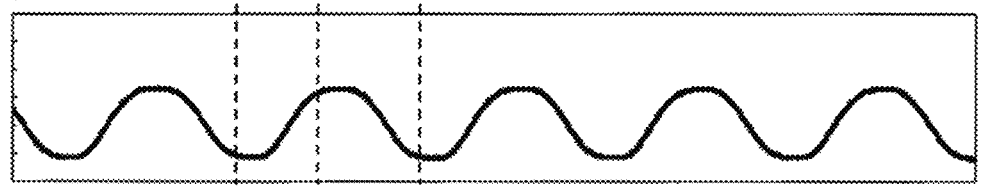
(c) FIRST-ORDER DIFFERENTIAL WAVEFORM
1204
1203
1201
1202
AVERAGE VALUE + WIDTH k × 0.3
AVERAGE VALUE
AVERAGE VALUE − WIDTH k × 0.3
(d) SECOND-ORDER DIFFERENTIAL WAVEFORM
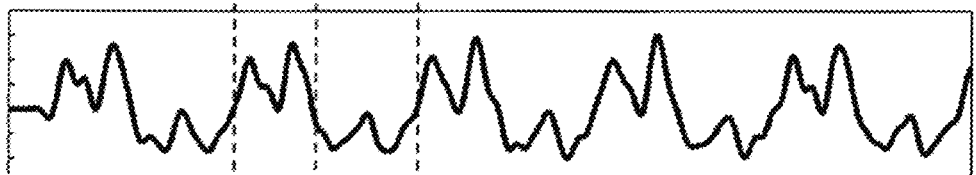
401 ASCENDING INTERVAL
402 DESCENDING INTERVAL

| VISCOSITY PROPERTY $G = V_p/V_l$ | 20'S | 30'S |
|---|---|---|
| 1 CM BELOW FACE/CHEEKBONES | 0.61 | 0.72 |
| BELOW FACE/CHEEKS | 0.65 | 0.74 |

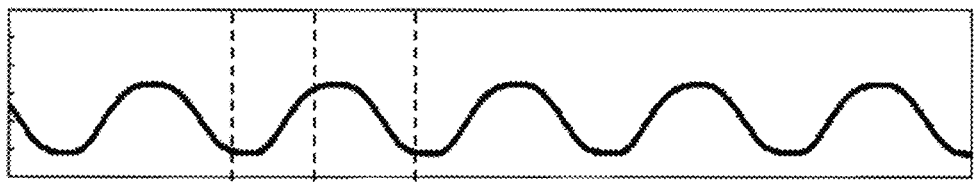
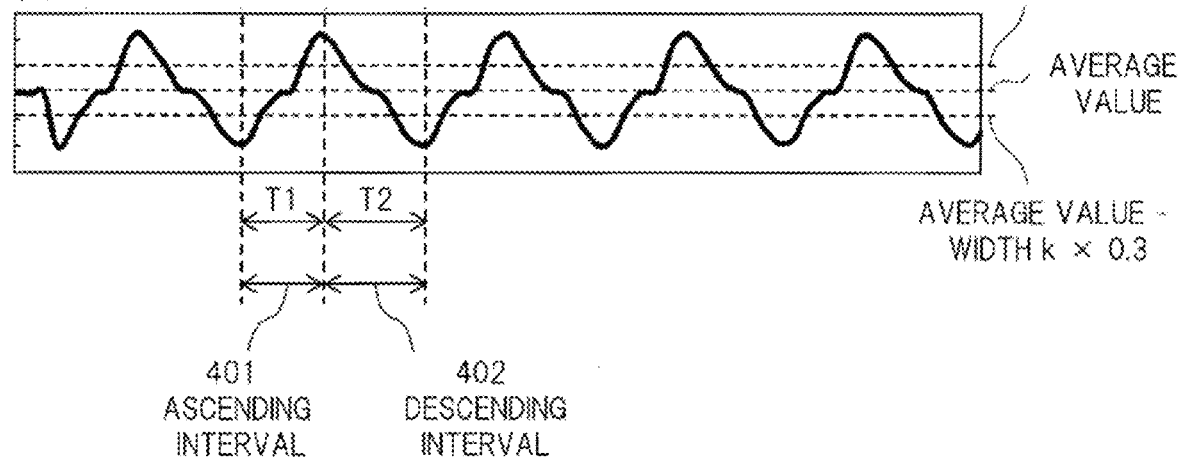

VISCOELASTICITY CALCULATION SYSTEM AND VISCOELASTICITY MEASUREMENT METHOD

CROSS-REFERENCE TO RELATED APPLICATION

This application is a Continuation of U.S. Ser. No. 15/577,085 filed on Nov. 17, 2017 which is a Bypass Continuation of International Patent Application No.: PCT/JP2016/061232 filed on Apr. 6, 2016, which claims priority to Japanese Patent Application No.: 2015-115086, filed on Jun. 5, 2015, the disclosure of which are incorporated herein in their entireties.

TECHNICAL FIELD

The present invention relates to a viscoelasticity calculation system and a viscoelasticity measurement method.

BACKGROUND ART

It is useful in many cases from conventionally to measure viscoelasticities of objects. When the object is a human body, viscoelasticity measurement is useful in a medical field, or skin orthopedic and cosmetic fields. In the medical field, for example, measuring the viscoelasticity of a predetermined portion makes it possible to determine an ulcer of a surface skin facing a bed due to a long-term bedridden state of taking the same position, a skin edema(s) and a scleroderma symptom(s) caused by an organic alteration(s), and the like. In addition, in the skin orthopedic and cosmetic fields, measuring the viscoelasticity of a predetermined portion makes it possible to determine a stage of progress of a disease(s), an effect of medication, and the like.

For example, there is a technique in which an apparatus including an acceleration sensor and a pressure sensor is pressed against an object such as a human body, thereby calculating hardness (elastic modulus) of the object by using a second-order differential of pressure information and acceleration information (see Patent Document 1).

In addition, there is a technique of contactlessly evaluating surface property such as elasticity of a skin by using a relationship between skin-surface displacement and time after momentarily injecting a compressed gas (see Patent Document 2).

RELATED ART DOCUMENTS

Patent Documents

Patent Document 1: Japanese Patent Application Laid-Open No. 2013-76658
Patent Document 2: Japanese Patent Application Laid-Open No. 2004-108794

SUMMARY OF THE INVENTION

Problems to be Solved by the Invention

It is, however, difficult to evaluate the viscoelasticity including viscosity and elasticity by pinching and picking up the skin of the human body. The conventional technique disclosed in Patent Document 1 is intended to calculate only the hardness (so-called elasticity), so that there is a problem of being unable to evaluate complex physical properties (viscoelasticity) of the human skin.

In addition, the technique disclosed in Patent Document 2 is intended to perform measurement at a position determined at a time of the measurement, and requires taking a complete rest of a measurement object. Furthermore, the technique disclosed in Patent Document 2 is intended to measure the displacement of the skin surface by one-time injection of the gas, but cannot measure dynamic viscoelasticity thereof.

Therefore, an abject of the present invention is to provide a technique of quantitatively measuring physical properties including both of viscosity and elasticity.

Means for Solving the Problems

For example, a configuration described in a scope of patent claims is adopted for solving the above problem. The present application includes a plurality of means for solving the above problem. To take one example thereof, however, provided is a viscoelasticity measurement system that calculates viscoelasticity of a measure object(s). The viscoelasticity measurement system includes a measurement apparatus, a processor, and a display apparatus. The measurement apparatus includes a movable unit continuously pressed against a measurement object, a first sensor outputting acceleration information corresponding to an acceleration of pressing-directional movement of a contact portion of the movable unit with respect to the measurement object, and a second sensor outputting reactive force information corresponding to a reactive force applied to the contact portion of the movable unit with respect to the measurement object. The processor calculates first information on an elasticity component of the measurement object and second information on a viscosity component of the measurement object based on the acceleration information and the reactive force information. The display apparatus displays the first information and the second information.

Effects of the Invention

According to the present invention, it is possible to quantitatively measure the physical properties including both of the viscosity and the elasticity. Further features associated with the present invention will become apparent from the description in this specification and the accompanying drawings. In addition, problems, arrangements, and effects other than those described above will become apparent from the description of the following embodiments.

BRIEF DESCRIPTIONS OF THE DRAWINGS

FIG. 12 is diagrams in which (a) shows an acceleration waveform, (b) shows a voltage waveform, (c) shows a first-order differential waveform of the voltage waveform, an average value of the first-order differential waveform, and positions spaced ±0.3 times a width of the first-order differential waveform apart from the average value, and (d) shows a second-order differential waveform;

FIG. 26 is a diagram showing a calculation processing of a viscosity component due to a voltage waveform.

DETAILED DESCRIPTION OF PREFERRED EMBODIMENTS

Figure 1:
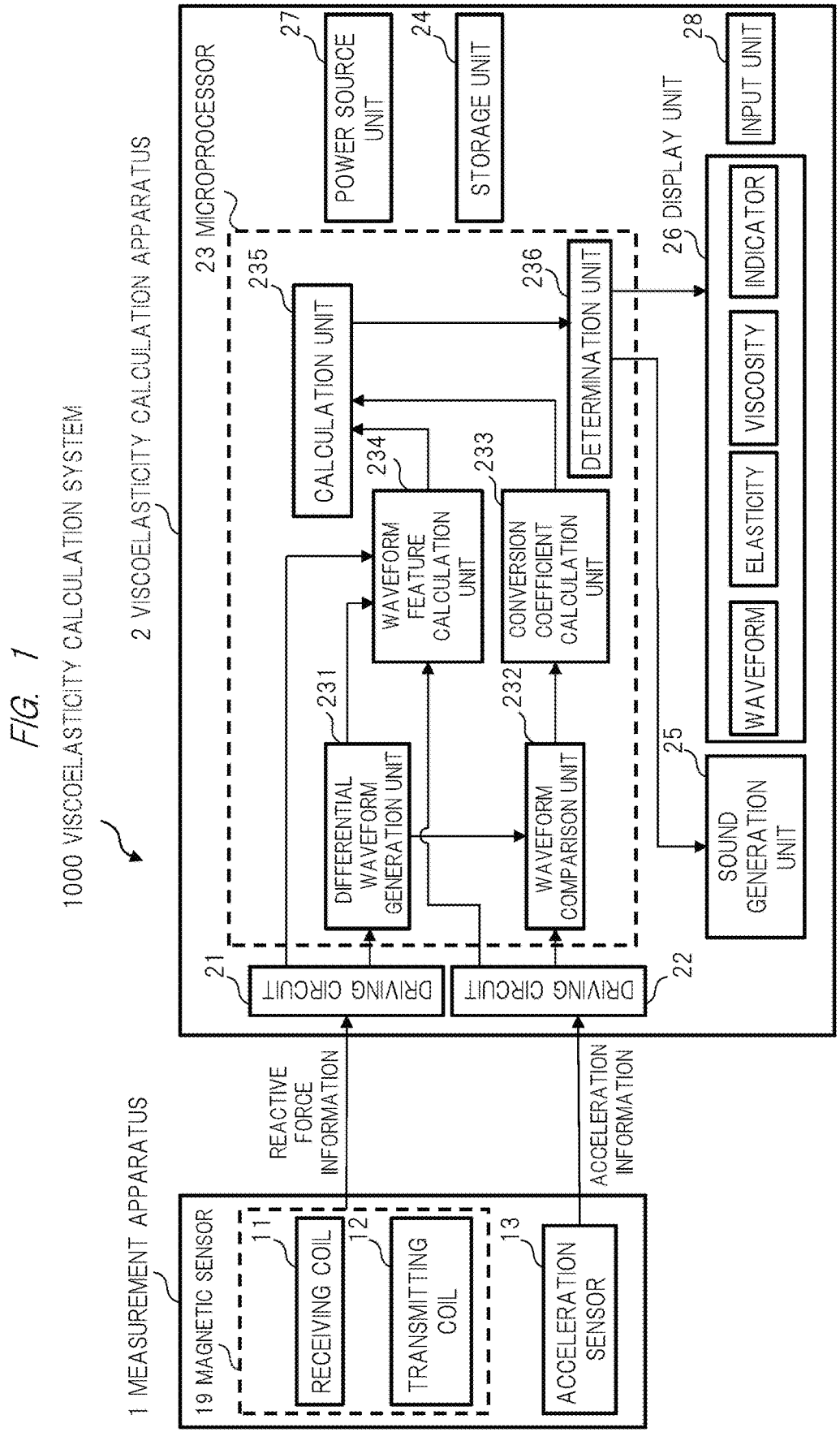
FIG. 1 is a diagram of the overall arrangement of a viscoelasticity calculation system according to an embodiment.

Embodiments of the present invention will be described below with reference to the accompanying drawings. Although the accompanying drawings show specific embodiments based on the principle of the present invention, they are provided for understanding of the present invention, and should not be used for limitedly interpreting the present invention. In addition, components common to the respective drawings will sometimes be denoted by the same reference numerals. Note that the following description sometimes is different in a unit scale such as "volt (V)" and "millivolt (mV)" for the sake of descriptive and illustrative convenience.

The following embodiments each relate to a technique of calculating viscoelasticity of a measurement object. Although the following description will exemplify a human body as a measurement object, the present invention is not limited to this. Measurement objects may include other objects such as food.

As described above, viscoelasticity is a concept including viscosity and elasticity. Elasticity represents a property in which an object, to which a force is applied and which is deformed, tries restoring its original shape when the force is removed. Viscosity represents a property in which the object is difficult to restore its original shape when deformed by applying the force thereto.

FIG. 1 is a diagram of the overall arrangement of a viscoelasticity calculation system. A viscoelasticity calculation system 1000 includes a measurement apparatus 1 and a viscoelasticity calculation apparatus 2. Note that the measurement apparatus 1 of FIG. 1 omits an illustration of part of its arrangement as compared with the measurement apparatus 1 shown in FIGS. 2 and 3.

Here, the arrangement and operation principle of the measurement apparatus 1 will be described with reference to FIG. 1 together with FIGS. 2 and 3. The measurement apparatus 1 includes: a main body unit 14 having a receiving coil 11 (magnetic field detection means); a movable unit 15 having a transmitting coil 12 (magnetic field generation means) and an acceleration sensor 13; and a spring 16 (elastic body). Note that a combination of the receiving coil 11 and the transmitting coil 12 will be referred to as a magnetic sensor 19. The magnetic sensor 19 outputs reactive force information corresponding to a reactive force applied to a contact portion of the movable unit with respect to an object. The acceleration sensor 13 outputs acceleration information corresponding to an acceleration of the pressing-directional movement of the contact portion of the movable unit with respect to the object.

A contact portion 20 is an area pressed against a trunk B of a human body so that the trunk B as an object is dented by an operator of the measurement apparatus 1 in calculating viscoelasticity. Note that the main body unit 14 and the movable unit 15 each have rigidity. The acceleration sensor 13 detects information about the acceleration of the pressing-directional movement. Here, the trunk B has a spring-like property and a dashpot-like property. For example, assume that the trunk B includes a spring 17(a) (spring constant K) and a dashpot 17(b) (dashpot constant G). The spring constant K and the dashpot constant G correspond to an elasticity component of the trunk B and a viscosity component of the trunk B, respectively. The elasticity component (first information) and the viscosity component (second information) are targets to be calculated in this embodiment.

The magnetic sensor 19 outputs information about a voltage equivalent to a magnitude of a reactive force of the trunk B, the reactive force corresponding to a pressure applied to the trunk B by the measurement apparatus 1. For this reason, the receiving coil 11 and the transmitting coil 12 are arranged to face each other. The spring 16 having a (known) spring constant K' is disposed between the main body unit 14 and the movable unit 15 (see FIG. 2). Note that the spring 16 is selected to satisfy a relation of K'>K. Otherwise, when a pressing force F is applied to the main body unit 14 (see FIG. 2), the main body unit 14 and the movable unit 15 come into contact with each other at the contact portion 20, thereby resulting in a loss of a role of the magnetic sensor 19. Incidentally, the measurement apparatus may be designed so that a distance D between the main body unit 14 and the movable unit 15 is set to about 2 mm, and a compression amount of the spring 16 is set to about 0.5 mm when the pressing force F is applied to the main body unit 14.

Note that the spring 16 may be replaced with a spring having the same shape and a larger wire diameter. In addition, the spring 16 may have a longer free length. Adopting these configurations will increase the pressing force F that allows the spring 16 to have the same compression amount, thereby also resulting in an increase in a force to be applied to the object from the main body unit 14. This makes it possible to measure a viscoelasticity at a deep position of the object. In a conventional technique, there has been a problem of only measuring elasticity and the like on a skin surface, and being unable to acquire information on a deep portion(s) from the skin surface. In contrast to this, the arrangement according to this embodiment makes it possible to measure not only the viscoelasticity of the skin surface but also the viscosity of subcutaneous tissue, muscle, and the like that exist deep beneath the skin surface.

Operations of the magnetic sensor 19 and its peripheral components will be described next with reference to FIG. 2. First of all, an AC oscillation source 31 generates an AC voltage having a specific frequency (for example, 20 kHz). An amplifier 32 converts the AC voltage into an AC current having a specific frequency. The converted AC current flows in the transmitting coil 12. A magnetic field generated by the AC current flowing in the transmitting coil 12 causes an induced electromotive force to be generated through the receiving coil 11.

A preamplifier 33 amplifies an AC current (having the same frequency as that of an AC voltage generated by the AC oscillation source 31) generated in the receiving coil 11 by the induced electromotive force. A signal after the amplification is inputted to a detection circuit 34. The detection circuit 34 detects the after-amplification signal by using a specific frequency generated by the AC oscillation source 31 or a double frequency. For this purpose, an output from the AC oscillation source 31 is introduced as a reference signal 35 to a reference signal input terminal of the detection circuit 34. Note that it is possible to use an operation scheme using a full-wave rectifying circuit without using the detection circuit 34. Voltage information (output signal) from the detection circuit 34 (or the rectifying circuit) is introduced to a driving circuit 21 (see FIG. 1) of the viscoelasticity calculation apparatus 2 after passing through a low-pass filter 36.

Figure 4:
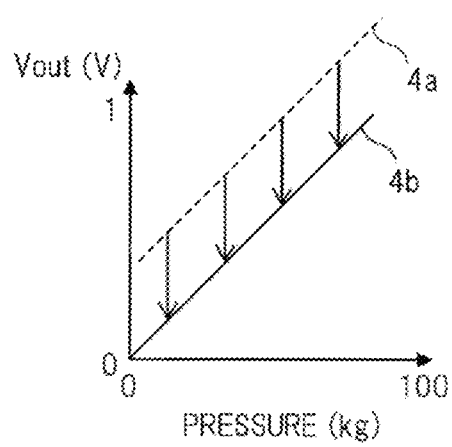
FIG. 4 is a diagram showing a relationship between an output voltage on a receiving coil side and a pressure due to compression.

Note that a line 4a (broken line) in FIG. 4 represents a relationship between the pressure (force F) applied to the main body unit 14 and the magnitude of the voltage represented by the output signal introduced to the driving circuit 21 from the low-pass filter 36. The line 4a is linear because the spring constant K' of the spring 16 is large, and the compression amount of the spring 16 with respect to the pressure against the main body unit 14 is small. By correcting the line 4a into a line 4b (solid line) so as to set the voltage to 0 when the pressure is 0, a relationship between pressure and voltage can be shifted to a proportional relationship passing through the origin. For example, a microprocessor 23 to be described later can perform this correction. In addition, assume that a conversion coefficient indicating a ratio of a pressure applied to the trunk B to the voltage information outputted from the magnetic sensor 19 will be referred to as a voltage/pressure conversion coefficient ($C_{mp}$[N/mV]) hereinafter, and a value of this coefficient is calculated in advance by experiments.

The viscoelasticity calculation apparatus 2 will be described next by referring back to FIG. 1. The viscoelasticity calculation apparatus 2 is a computer apparatus. The viscoelasticity calculation apparatus 2 includes the driving circuit 21, a driving circuit 22, the microprocessor 23, a storage unit 24, a sound generation unit 25, a display unit 26, a power source unit 27, and an input unit 28.

The driving circuit 21 transmits, to the microprocessor 23, the voltage information received from the receiving coil 11 of the measurement apparatus 1 via the low-pass filter 36 (see FIG. 2) etc. The driving circuit 22 transmits, to the microprocessor 23, the acceleration information received from the acceleration sensor 13 of the measurement apparatus 1.

The microprocessor 23 is implemented by, for example, a central processing unit (CPU). The microprocessor 23 includes a differential waveform generation unit 231, a waveform comparison unit 232, a conversion coefficient calculation unit 233, a waveform feature calculation unit 234, a calculation unit 235, and a determination unit 236. The above processing units of the microprocessor 23 can be implemented by various types of programs. For example, various types of programs stored in the storage unit 24 are loaded into a memory (not shown) in the viscoelasticity calculation apparatus 2. The microprocessor 23 executes the programs loaded into the memory. A content of a processing executed by each processing unit of the microprocessor 23 will be described with reference to FIGS. 5 to 7.

Figure 5:
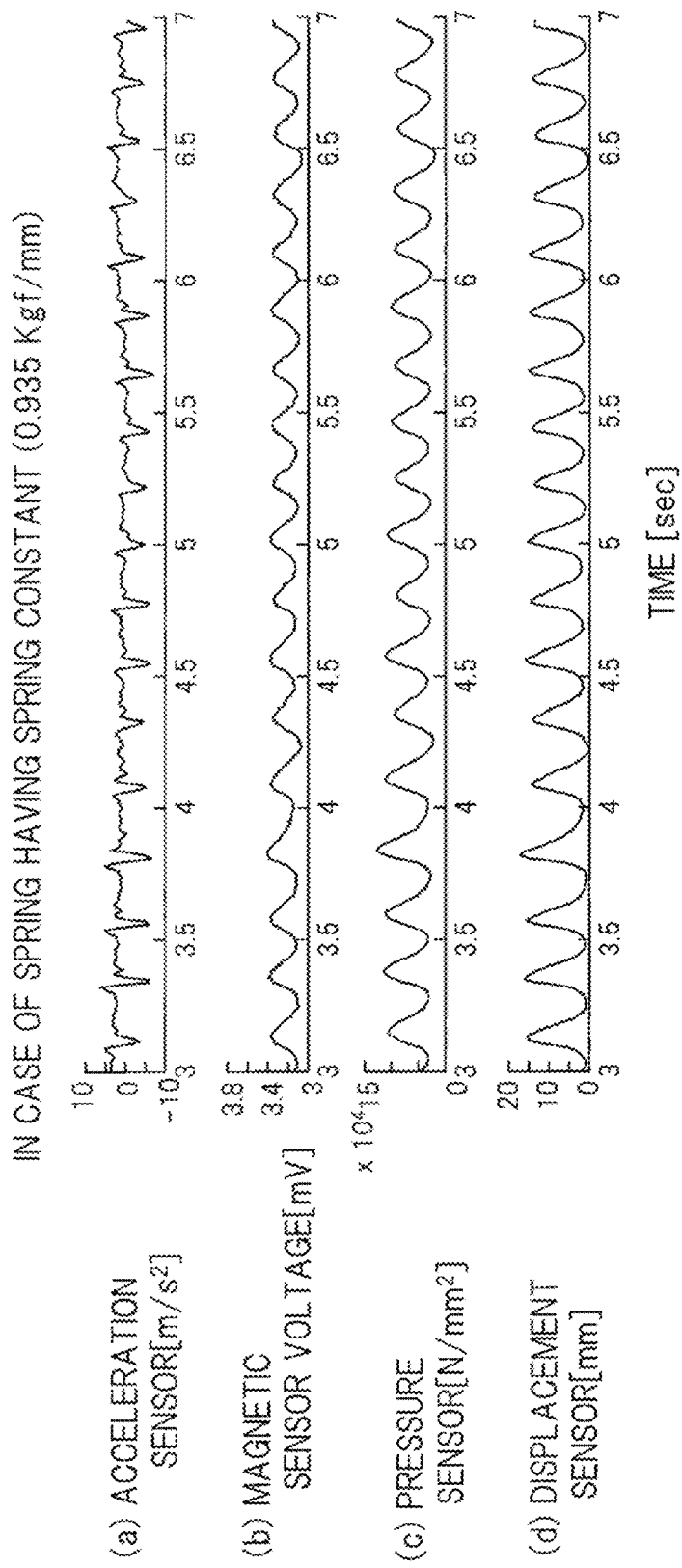
FIG. 5 is diagrams in which an object is set at a spring, (a) showing an output from an acceleration sensor, (b) showing an output from a magnetic sensor, (c) showing an output from a pressure sensor, and (d) showing an output from a displacement sensor.

As shown in FIG. 5, in a case of using a spring having a spring constant of 0.935 kgf/mm, (a) represents an output from the acceleration sensor 13, (b) represents an output from the magnetic sensor 19, (c) represents an output from a pressure sensor (not shown) used in place of the magnetic sensor 19, and (d) represents an output (a true value (correct value) of displacement) from a displacement sensor (not shown) such as a laser sensor as a reference.

Figure 2:
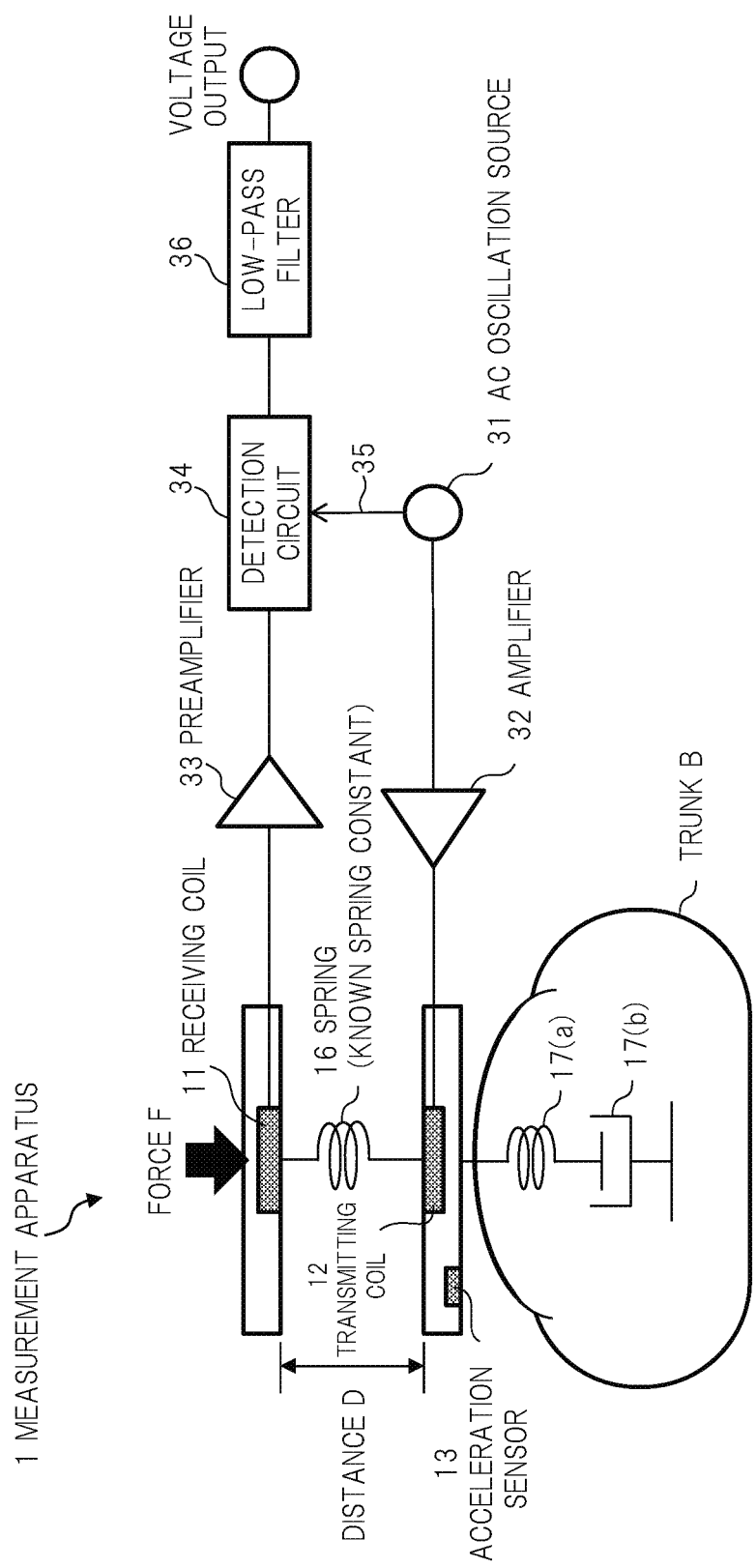
FIG. 2 is an explanatory diagram of an operation principle of a measurement apparatus.
Figure 3:
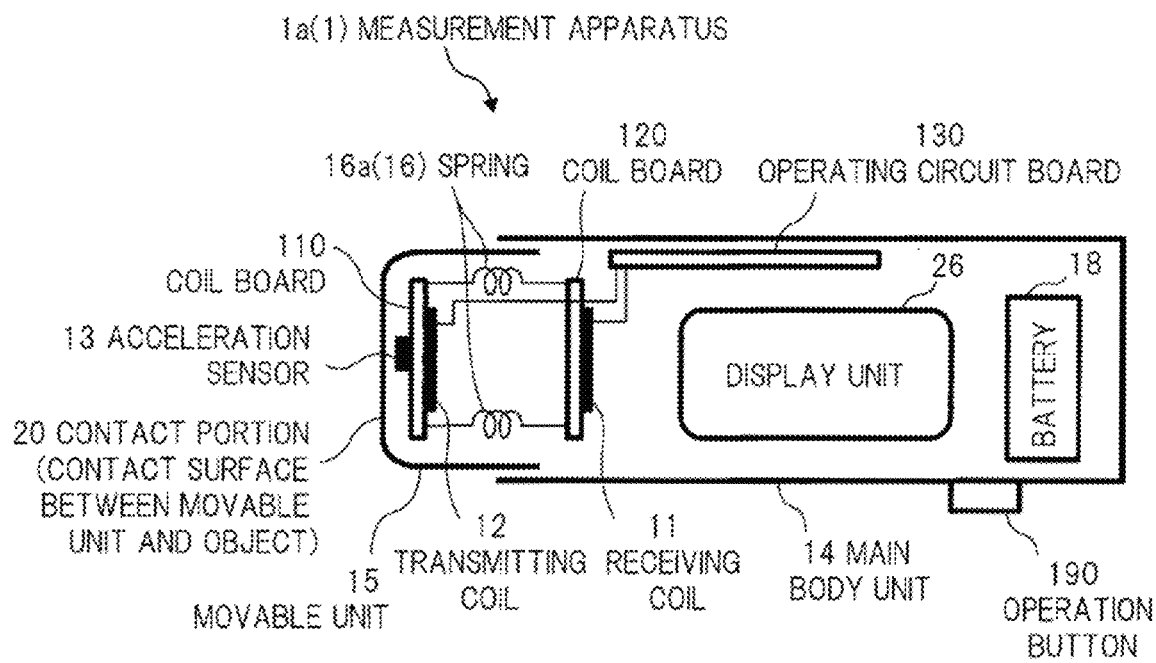
FIG. 3 is a schematic view of an example of a structure of the measurement apparatus.

Note that an object of this embodiment is to calculate the viscoelastic modulus (viscosity component and elasticity component) of the object, that is, calculate the spring constant K and the dashpot constant G in FIG. 2. For this purpose, consider first that information as approximated to information represented by (d) as possible is obtained by using at least one or more pieces of output information represented by (a), (b), and (c) in FIG. 5. The elasticity component and the viscosity component of the object are calculated by using the obtained information.

That is, in order to calculate the viscoelasticity feature of the object without using a displacement sensor such as a laser sensor, the information obtained by the acceleration sensor 13 and the magnetic sensor 19 (or the pressure sensor) is used. The reasons why the displacement sensor is not used include, for example, a surface condition of the object, difficulty in use due to whether the sensor is fixable to the object, and expensiveness, etc.

Referring to FIG. 5, when the waveform outputted from the magnetic sensor 19 and represented by (b) is compared with the waveform outputted from the displacement sensor and represented by (d), they differ in unit on a longitudinal axis and magnitude of an amplitude, but much resemble each other in outline shape. In addition, these waveforms have the same frequency. Consequently, when the waveform outputted from the magnetic sensor 19 and represented by (b) is multiplied by a predetermined conversion coefficient (to be referred to as a "voltage/displacement conversion coefficient ($C_{md}$[mm/mV])" hereinafter), information on a waveform approximated to the waveform outputted from the displacement sensor and represented by (d) can be obtained. The voltage/displacement conversion coefficient $C_{md}$ is a numerical value representing a ratio of a magnitude of each acceleration waveform to a second-order differential waveform (to be described in detail later). Note that the same applies to the waveform outputted from the pressure sensor and represented by (c), and the waveform outputted from the displacement sensor and represented by (d).

Here, the calculation of the viscoelastic modulus of the object will be described with reference to equations (see the drawings appropriately). It is assumed that X is compression amounts (displacement amounts) of the spring 17(a) and the dashpot 17(b) when the pressing force (pressure) F is applied to the main body unit 14 (see FIG. 2), and that $V_m$ is an output voltage from the magnetic sensor 19, equations (1), (2), and (3) are satisfied. Note that according to the action-reaction law, the force (pressure) F is applied also to the contact portion 20 between the movable unit 15 and the trunk B.

[Math 1]

$$F = K \times X \quad \text{Equation (1)}$$

$$X = C_{md} \times V_m \quad \text{Equation (2)}$$

$$F = C_{mp} \times V_m \quad \text{Equation (3)}$$

Equation (1) is an equation representing Hooke's law, equation (2) is an equation representing that the displacement amount X can be obtained by multiplying the output voltage $V_m$ from the magnetic sensor 19 by the voltage/displacement conversion coefficient $C_{md}$, and equation (3) is an equation representing that the pressure F can be obtained by multiplying the output voltage $V_m$ from the magnetic sensor 19 by the voltage/pressure conversion coefficient $C_{mp}$.

Equation (4) given below can be obtained by substituting equations (2) and (3) into equation (1) and rearranging equation (1).

[Math 2]

$$K = \frac{C_{mp}}{C_{md}} \quad \text{Equation (4)}$$

That is, the complex elastic modulus of the object can be calculated by dividing the voltage/pressure conversion coefficient $C_{mp}$ by the voltage/displacement conversion coefficient $C_{md}$.

Referring back to FIG. 1, the storage unit 24 is a means for storing various types of information, and is realized by, for example, a random access memory (RAM), read only memory (ROM), hard disk drive (HDD), or the like. The storage unit 24 stores in advance the voltage/pressure conversion coefficient $C_{mp}$ calculated by an experiment(s).

The sound generation unit 25 is a means for generating a sound(s), and is realized by, for example, a loudspeaker. The sound generation unit 25 generates a beep sound, for example, when the measurement apparatus 1 starts or ends the measurement.

The display unit 26 is a means for displaying various types of information, and is realized by, for example, a liquid crystal display (LCD) or cathode ray tube (CRT) display. The display unit 26 displays, for example, indicators etc. as visualizing various waveforms, viscosity of an object, elasticity of the object, and viscoelasticity of the object.

The power source unit 27 is a power source supply means in the viscoelasticity calculation apparatus 2. The input unit 28 is a means to be operated by the user for inputting various types of information, and is realized by, for example, a keyboard and a mouse, etc.

Here, an example of the structure of the measurement apparatus 1 will be described below with reference to FIG. 3. Note that descriptions of particulars described with reference to FIG. 2 will be omitted appropriately. A measurement apparatus 1a(1) has a pencil shape as a whole. The measurement apparatus 1a(1) is constituted by the main body unit 14 and the movable unit 15.

The main body unit 14 includes: the receiving coil 11; a coil board 120 on which the receiving coil 11 is mounted; an operating circuit board 130 connected to the receiving coil 11 and the transmitting coil 12; a battery 18; an operation button 190 to be operated at a time of starting etc. hardness calculation; and the display unit 26. The movable unit 15 includes: the transmitting coil 12; the acceleration sensor 13; and a coil board 110 on which the transmitting coil 12 and the acceleration sensor 13 are mounted.

One to four springs 16a(16) are arranged between the coil board 110 and the coil board 120. Used as a simple scheme can be one spring 16a(16) having a diameter equal to or more than each coil diameter of the coil board 110 and the transmitting coil 12. If the one spring 16a(16) is regarded as a single configuration, a coil of the coil board 110 and the transmitting coil 12 can be disposed inside the spring 16a(16). This enables downsizing of the apparatus.

According to the measurement apparatus 1a(1), when the movable unit 15 is pressed against an object so that the object dents, the spring 16a(16) is compressed to make the transmitting coil 12 approach the receiving coil 11, and a magnitude of a magnetic field detected by the receiving coil 11 is increased. Therefore, the receiving coil 11 outputs information on a voltage corresponding to a magnitude of the reactive force generated at the contact portion 20. In addition, since the measurement apparatus 1a(1) has a pencil shape as a whole, it is compact and is easy to use.

Figure 7:
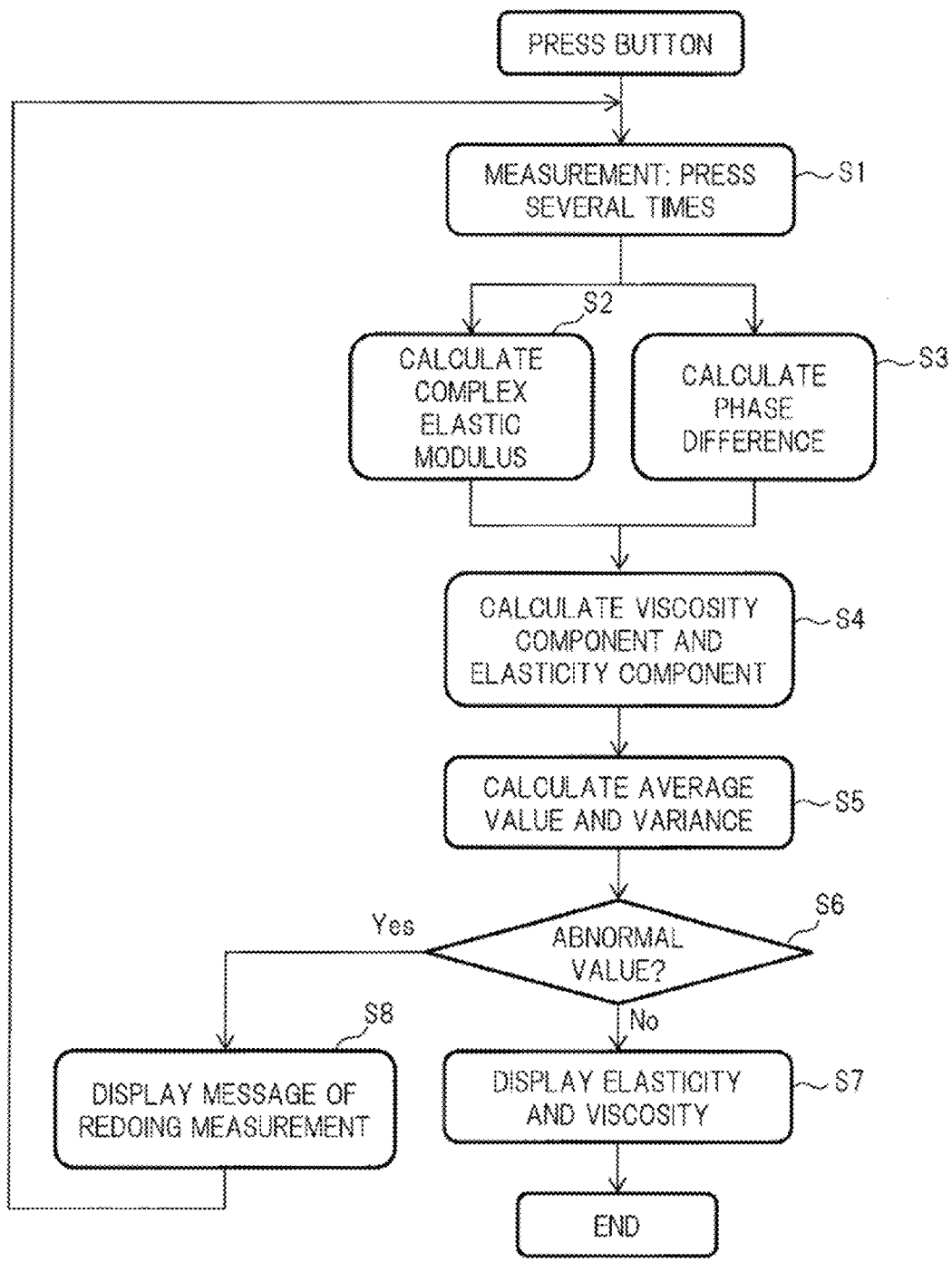
FIG. 7 is an example of a flowchart showing a flow of the overall processings in a viscoelasticity calculation system (first embodiment)

A processing by the viscoelasticity calculation system 1000 will be described next with reference to a flowchart of FIG. 7 (see other drawings appropriately).

First of all, an operator operates an operation button 190 of the measurement apparatus 1. Subsequently, in this case, the operator continuously presses, several times, the movable unit 15 of the measurement apparatus 1 against the object at a frequency fHz (step S1). In this case, the movable unit 15 of the measurement apparatus 1 manually pressed against a contact region of the object, and then is released. Those operations of the pressing and the releasing are repeated. Alternatively, the overall measurement apparatus 1 may be attached to a motor (not shown). In this arrangement, by driving the motor, the movable unit 15 is continuously pressed against the object at the frequency fHz. Note that the frequency f may be set to a degree of several Hz to several tens Hz. Note that the frequency f may be changed appropriately depending on an object to be measured. When viscoelasticity of the human skin is to be measured, the frequency f is preferably set to a degree of 2 Hz to 10 Hz.

Figure 17:
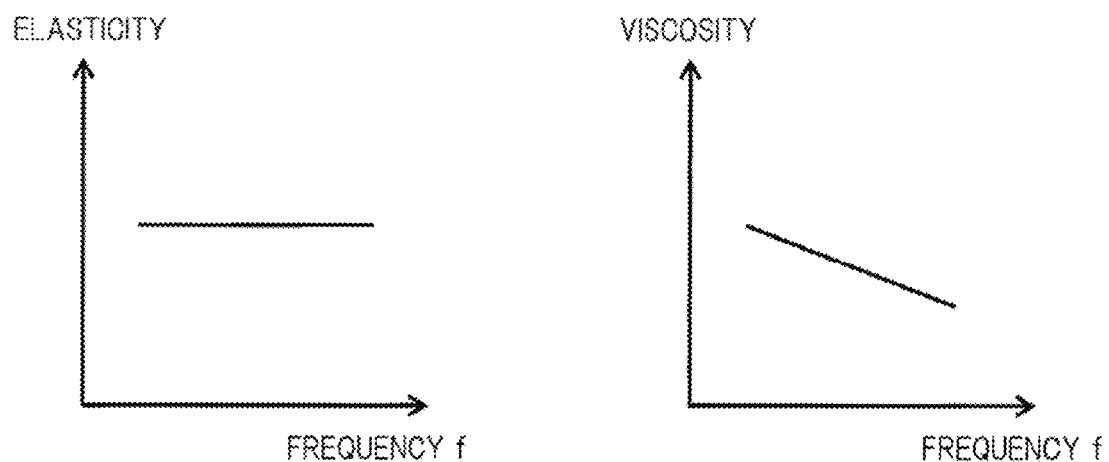
FIG. 17 is a diagram showing a relationship between frequency and elasticity and a relationship between frequency and viscosity.

Thus, to set the frequency f in accordance with a measurement object is for the following reason. FIG. 17 shows a relationship between frequency and elasticity, and a relationship between frequency and viscosity. As shown in FIG. 17, when the frequency f increases, information on an elasticity component does not change. In contrast, information on dynamic viscosity property may significantly decrease when the frequency f increases. Even if the measurement object has low viscosity (that is, an object that quickly restores its original shape), increasing the frequency f will make the measurement apparatus 1 pressed against the object before restoring its original shape. This makes it difficult to obtain information on a displacement between pressing of the measurement apparatus 1 and releasing thereof. Thus, increasing the frequency f sometimes makes it difficult to obtain the information on the viscosity property. For this reason, the frequency f is preferably set within a predetermined range in accordance with the measurement object.

Figure 18:
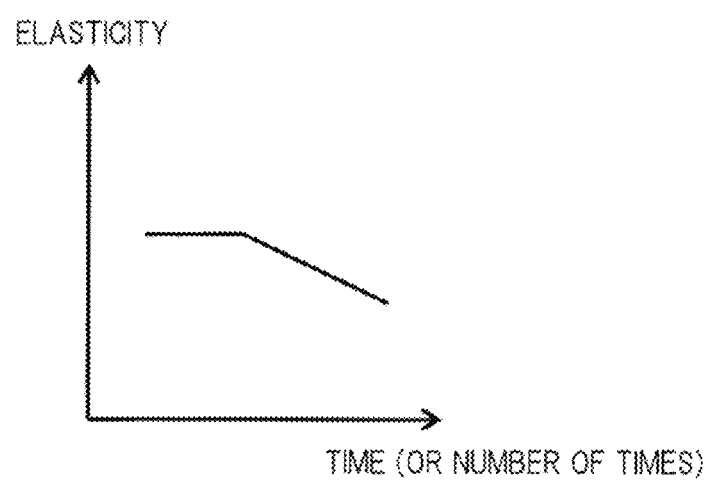
FIG. 18 is a diagram showing a relationship between time (or number of measurement times) and elasticity.

In addition, as shown in FIG. 18, if the measurement time increases or the number of times of the measurement increases depending on the measurement object, the viscoelasticity properties (the example of FIG. 18 shows only the elasticity) become significantly weak. Therefore, the measurement time and the number of times of the measurement are preferably set within the predetermined range in accordance with the measurement object.

The microprocessor 23 of the viscoelasticity calculation apparatus 2 acquires information from the measurement apparatus 1 every time the movable unit 15 of the measurement apparatus 1 is pressed against the object. The microprocessor 23 calculates a complex elastic modulus on the basis of the information (reactive force information and acceleration information) acquired from the measurement apparatus 1 (step S2). Incidentally, the microprocessor 23 calculates a phase difference on the basis of information (reactive force information and acceleration information) acquired from the measurement apparatus 1 (step S3). Incidentally, although steps S2 and S3 in FIG. 7 are executed in parallel, the present invention is not limited to this method. Steps S2 and S3 may be sequentially executed. The details of steps S2 and S3 will be described later with reference to FIGS. 8 and 9.

The microprocessor 23 calculates an elasticity component(s) and a viscosity component(s) on the basis of the calculated complex elastic modulus and phase difference (step S4). Then, the microprocessor 23 calculates an average value and a variance about elasticity component data and viscosity component data calculated in step S4 (step S5).

The microprocessor 23 then determines, on the basis of the average value and the variance calculated in step S5, whether these values are abnormal values (step S6). The determination unit 236 of the microprocessor 23 executes this processing. If YES, the process advances to step S7. If NO, the process advances to step S8. Note that the determination of whether the average value and the variance are abnormal values can be realized by comparing them with preset thresholds.

In addition, selection of YES at step S6 (if the average value and the variance are abnormal values) is considered that accuracy of acceleration detection of the acceleration sensor 13 degrades by, for example, shaking a hand(s) holding the measurement apparatus 1. When the process advances to step S8, the microprocessor 23 causes the display unit 26 to display a message of redoing the measurement. The process then returns to step S1.

When the process advances to step S7, the microprocessor 23 causes the display unit 26 to display information on the viscosity component and information on the elasticity component, and terminates this processing. In this case, since the movable unit 15 of the measurement apparatus 1 is pressed against the object a plurality of number of times, information on a plurality of elasticity components and information on a plurality of viscosity components can be acquired by the calculation in step S4. As an example, the display unit 26 may display an average value(s) of the information on the viscosity components and an average value(s) of information on the elasticity components.

First Embodiment

Figure 8:
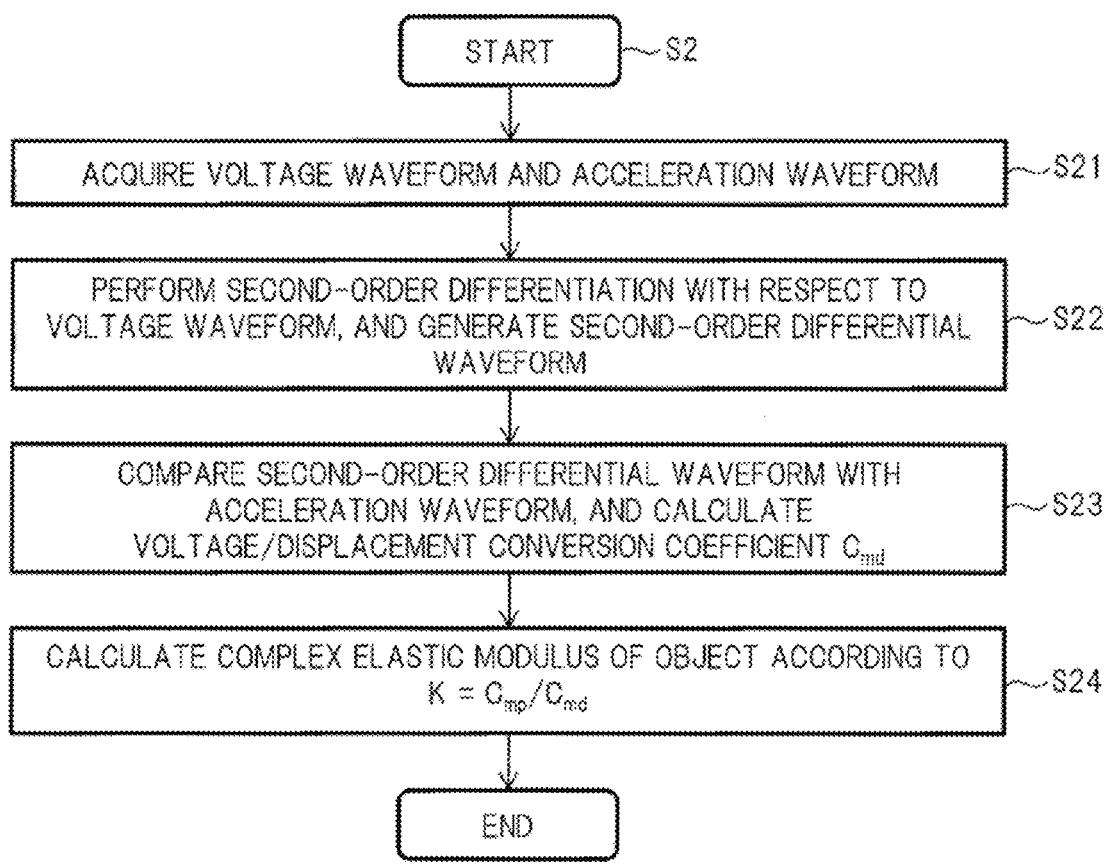
FIG. 8 is a flowchart showing a flow of processings in step S2 of FIG. 7 (complex elastic modulus calculation)
Figure 9:
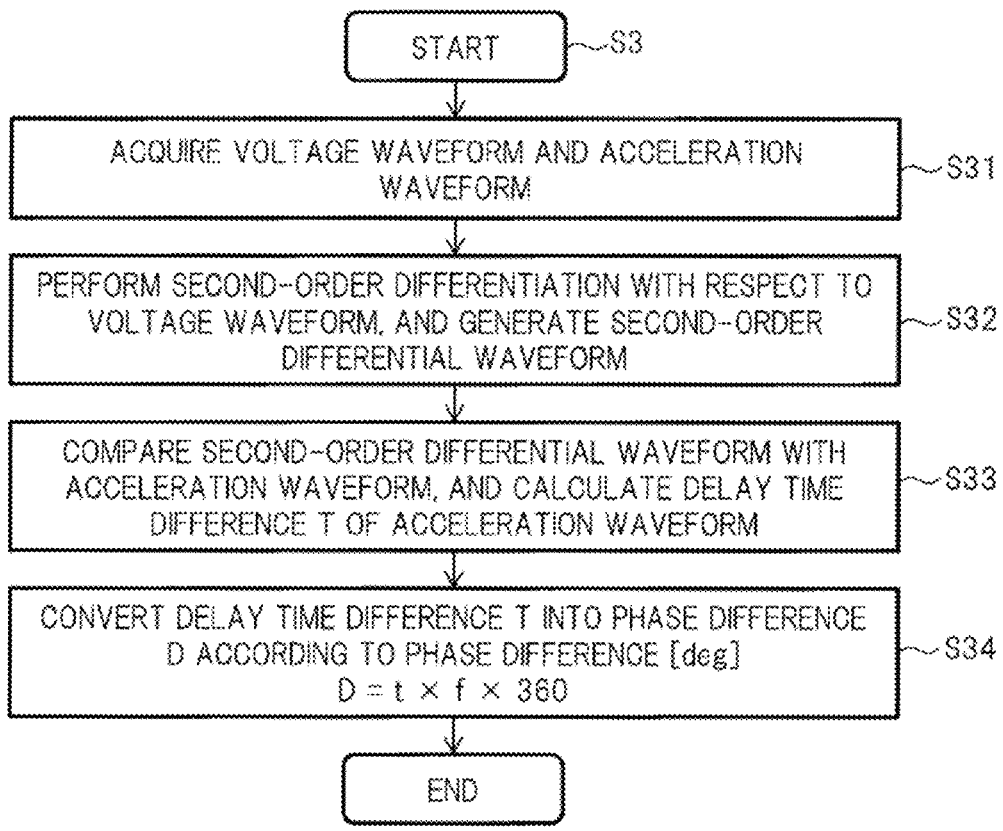
FIG. 9 is a flowchart showing a flow of processings in step S3 of FIG. 7 (phase difference calculation)

Processings in steps S2 and S3 will be described next with reference to the flowcharts of FIGS. 8 and 9. Incidentally, FIG. 7 explains that the information on the plurality of elasticity components and the information on the plurality of viscosity components can be acquired, but the flowcharts of FIGS. 8 and 9 will explain one-time calculation of a viscosity component(s) and an elasticity component(s).

Figure 6:
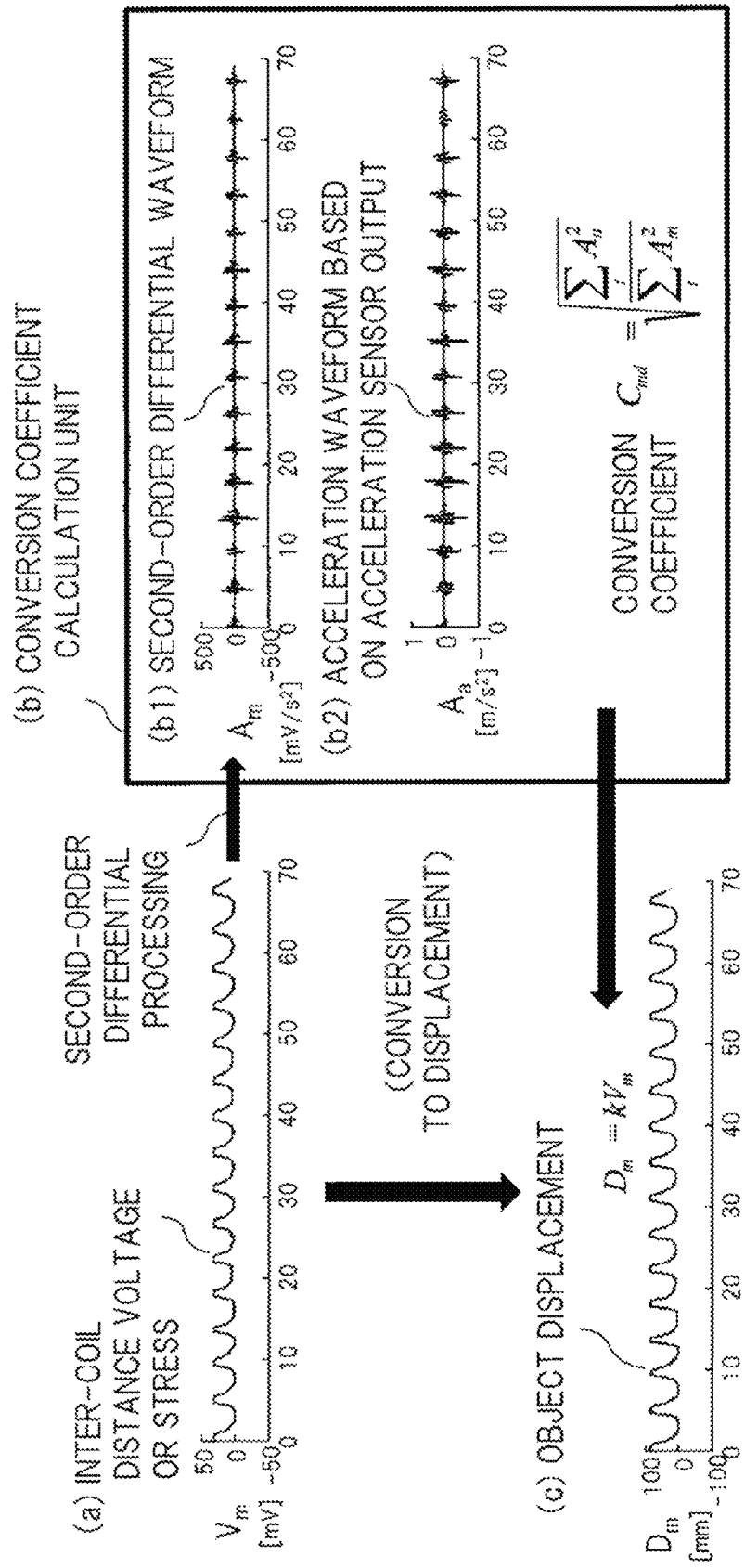
FIG. 6 is diagrams in which (a) shows a magnetic sensor voltage, (b1) shows a second-order differential waveform, (b2) shows an acceleration waveform based on an output from an acceleration sensor, and (c) shows a displacement of an object.

A calculation processing of a complex elastic modulus (step S2) will be described first with reference to FIG. 8. The microprocessor 23 acquires a voltage waveform based on information on the voltage acquired from the magnetic sensor 19 via the driving circuit 21, and an acceleration waveform based on information on the acceleration acquired from the acceleration sensor 13 via the driving circuit 22 (step S21). The voltage waveform is inputted to a differential waveform generation unit 231. The acceleration waveform is inputted to a waveform comparison unit 232. In FIG. 6, (a) represents the voltage waveform. In FIG. 6, (b2) represents the acceleration waveform.

The differential waveform generation unit 231 then performs second-order differentiation with respect to the voltage waveform to generate a second-order differential waveform (step S22). In FIG. 6, (b1) represents the second-order differential waveform calculated from the voltage waveform.

The waveform comparison unit 232 then compares the second-order differential waveform ((b1) in FIG. 6) calculated by the differential waveform generation unit 231 with the acceleration waveform ((b2) in FIG. 6), and outputs a comparison result to a conversion coefficient calculation unit 233. The conversion coefficient calculation unit 233 calculates a voltage/displacement conversion coefficient $C_{md}$ on the basis of the comparison result (step S23).

More specifically, the voltage/displacement conversion coefficient $C_{md}$ can be calculated by using equation (5) given below (see (b) in FIG. 6). Am and Aa in equation (5) respectively correspond to values indicated by (b1) and (b2) in FIG. 6. Then, by converting the voltage waveform of FIG. 6(a) using the voltage/displacement conversion coefficient Cmd, the displacement waveform of the object can be obtained (FIG. 6(c)).

[Math 3]

$$C_{md} = \sqrt{\frac{\sum_t A_a^2}{\sum_t A_m^2}}$$

Equation (5)

The conversion coefficient calculation unit 233 then divides a voltage/pressure conversion coefficient $C_{mp}$ stored in the storage unit 24 in advance by the voltage/displacement conversion coefficient $C_{md}$ (see equation (4)), thereby calculating an absolute value K of the complex elastic modulus of the object (step S24). A complex elastic modulus is a dynamic physical property value of a material, which takes into account energy lost as heat when a viscoelastic body deforms and restores its shape. The real part and the imaginary part of the complex elastic modulus are respectively equivalent to a storage elastic modulus and a loss elastic modulus.

A calculation processing of the phase difference (step S3) will be described next with reference to FIG. 9. The microprocessor 23 acquires a voltage waveform based on information on the voltage acquired from the magnetic sensor 19 via the driving circuit 21, and an acceleration waveform based on information on the acceleration acquired from the acceleration sensor 13 via the driving circuit 22 (step S31). The voltage waveform is inputted to the differential waveform generation unit 231. The acceleration waveform is inputted to the waveform feature calculation unit 234. In FIG. 12, (a) shows an acceleration waveform. In FIG. 12, (b) shows a voltage waveform.

The differential waveform generation unit 231 then generates a second-order differential waveform by performing second-order differentiation with respect to the voltage waveform (step S32). The differential waveform generation unit 231 outputs the second-order differential waveform to the waveform feature calculation unit 234. In FIG. 12, (d) shows the second-order differential waveform calculated from the voltage waveform.

The waveform feature calculation unit 234 then calculates a delay time difference T between the second-order differential waveform and the acceleration waveform (step S33). Examples of the calculation processing in step S33 will be described below.

First Example

Cross-Correlation

An example of step S33 will be described. The waveform feature calculation unit 234 flips (reverses) order of one of a data array of the second-order differential waveform and a data array of the acceleration waveform, and convolutes the two data arrays to obtain a cross-correlation function. The waveform feature calculation unit 234 then detects the maximum peak of the cross-correlation function, and estimates a time difference at a point corresponding to the maximum peak to be the delay time difference T between the second-order differential waveform and the acceleration waveform. The waveform feature calculation unit 234 outputs the delay time difference T to a calculation unit 235. Incidentally, by the continuous pressing frequency f, the delay time difference T is equal to or less than $(1/4) \times (1/f)$ (that is, the phase difference is 90° at the maximum). According to the first example, the delay time difference T can be obtained by a simple processing.

Second Example

Cross-Power Spectrum Phase

Figure 10:
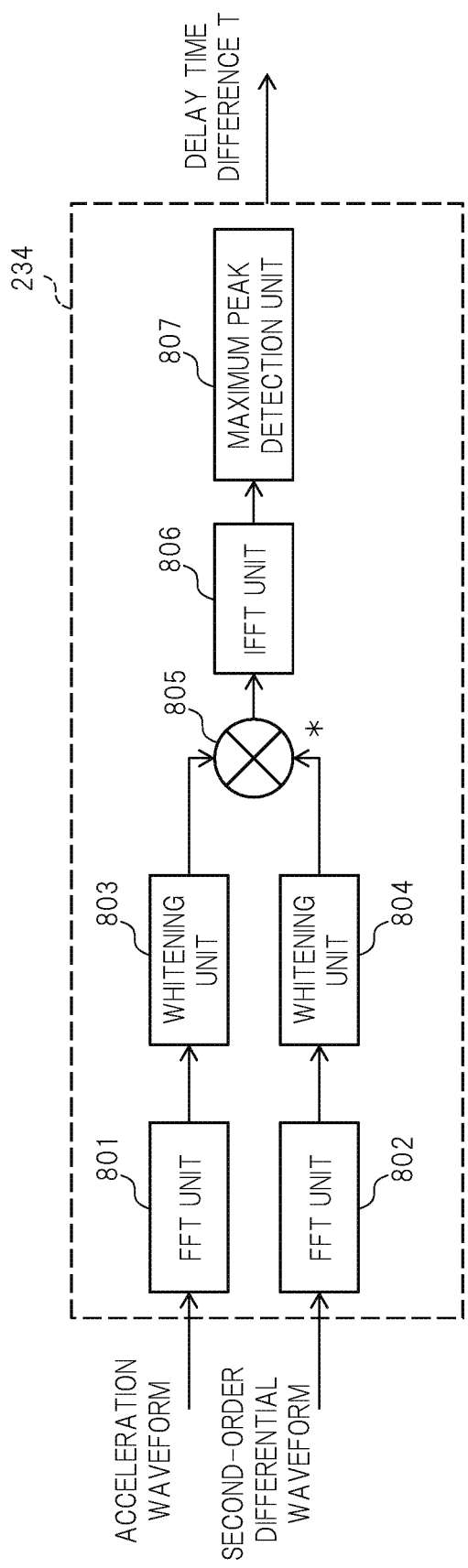
FIG. 10 is an example of a functional block of a waveform feature calculation unit, and a functional block diagram of a delay time difference calculation processing based on a cross-power spectrum phase coefficient.

An example of step S33 will be described. FIG. 10 shows an example of a functional block of the waveform feature calculation unit 234. The waveform feature calculation unit 234 includes FFT units 801 and 802, whitening units 803 and 804, a multiplying unit 805, an IFFT unit 806, and a maximum peak detection unit 807.

The FFT units 801 and 802 convert each of second-order differential waveform data and acceleration waveform data into frequency domain data. The whitening units 803 and 804 whiten (flatten) signals converted into a frequency domain by using frequency spectra.

The multiplying unit 805 obtains a cross-spectrum by conjugating only one of the whitened signals and multiplying the two signals for each frequency component. The IFFT unit 806 converts an output signal (cross-spectrum) from the multiplying unit 805 into a time domain, and obtains a cross-power spectrum phase. The maximum peak detection unit 807 then detects the maximum peak of the cross-power spectrum phase outputted from the IFFT unit 806, and estimates a time difference at a point corresponding to the maximum peak to be the delay time difference T between the second-order differential waveform and the acceleration waveform. The waveform feature calculation unit 234 outputs the delay time difference T to the calculation unit 235. According to the second example, by obtaining a cross-power spectrum phase, the delay time difference T can be obtained even if the second-order differential waveform does not completely match the acceleration waveform.

Third Example

Pickup of Peak

Figure 11:
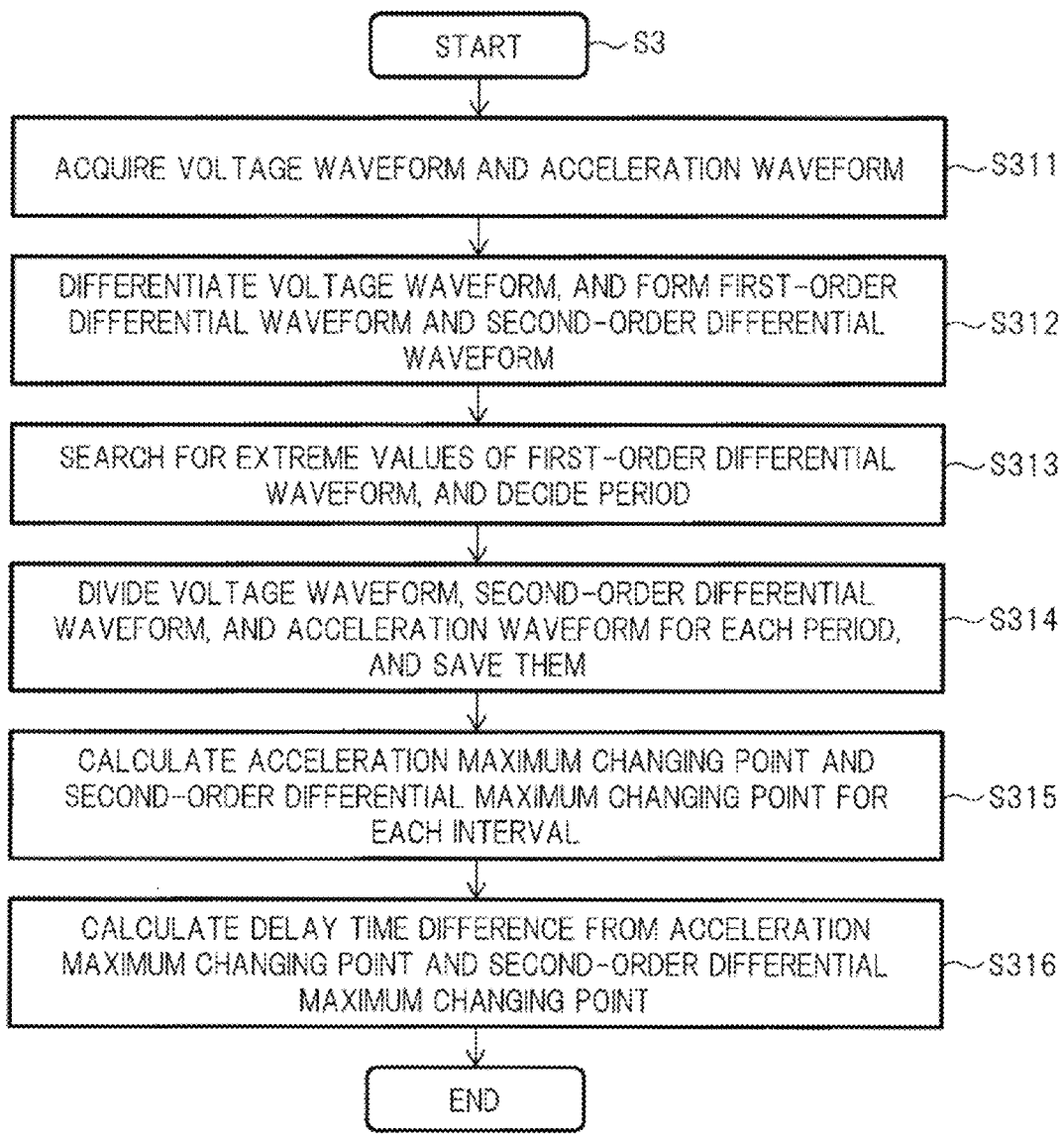
FIG. 11 is a flowchart for explaining a delay time difference calculation processing by position detection at a peak.

Another example of step S3 will be described. FIG. 11 is a flowchart for explaining a calculation processing of a delay time difference T.

The microprocessor 23 acquires a voltage waveform based on information on a voltage acquired from the magnetic sensor 19 via the driving circuit 21, and an acceleration waveform based on information on an acceleration acquired from the acceleration sensor 13 via the driving circuit 22 (step S311). The voltage waveform is inputted to the differential waveform generation unit 231. The acceleration waveform is inputted to the waveform feature calculation unit 234. In FIG. 12, (a) shows the acceleration waveform. In FIG. 12, (b) shows the voltage waveform.

The differential waveform generation unit 231 then generates a first-order differential waveform and a second-order differential waveform from the voltage waveform (step S312). The differential waveform generation unit 231 outputs the first-order differential waveform and the second-order differential waveform to the waveform feature calculation unit 234. In FIG. 12, (c) shows the first-order differential waveform of the voltage waveform, and (d) shows the second-order differential waveform of the voltage waveform.

The waveform feature calculation unit 234 searches for extreme values of the first-order differential waveform, and decides a period (step S313). A period decision method will be described in detail below. First of all, the waveform feature calculation unit 234 calculates an average value of the first-order differential waveform. The waveform feature calculation unit 234 then calculates an average value of the first-order differential waveform, calculates an amplitude k of the first-order differential waveform, and calculates a value of 0.3 times the amplitude k. In this case, the value by which the amplitude k is multiplied is set at 0.3. However, the present invention is not limited to this value. The value may be appropriately changed as long as it is possible to search for an extreme value(s) of a first-order differential waveform as described below.

The waveform feature calculation unit 234 then searches for data smaller than (average−amplitude k×0.3) from data on the first-order differential waveform, and saves the searched continuous data as one interval. In FIG. 12, a broken line 1201 in (c) represents an interval smaller than (average value−amplitude k×0.3). The waveform feature calculation unit 234 obtains the minimum value of each interval 1201, and saves the position of the minimum value as a period dividing point of the first-order differential waveform. In FIG. 12, a point 1202 in (c) indicates the minimum value in the interval 1201.

The waveform feature calculation unit 234 then searches for data larger than (average value−amplitude k×0.3) from data on the first-order differential waveform, and saves the searched continuous data as one interval. In FIG. 12, a broken line 1203 in (c) indicates an interval larger than (average value−amplitude k×0.3). The waveform feature calculation unit 234 obtains the maximum value of each interval 1203, and saves the position of the maximum value as a period midpoint of the voltage waveform. Therefore, a period of the voltage waveform can be defined by an ascending interval 401 and a descending interval 402 between two period dividing points (minimum values 1202).

The waveform feature calculation unit 234 then divides the acceleration waveform, the voltage waveform, and the second-order differential waveform for each period in accordance with the period dividing points, and saves the divided waveforms (step S314). As described above, with regard to the voltage waveform, an interval from a period start point to the period midpoint is called the ascending interval 401, and an interval from the period midpoint to a period end point is called the descending interval 402.

The waveform feature calculation unit 234 then calculates the maximum changing point of the acceleration waveform and the maximum changing point of the second-order differential waveform for each interval of the period (step S315). Incidentally, since the same calculation is performed for each interval, the calculation in one interval will be described below.

Figure 13:
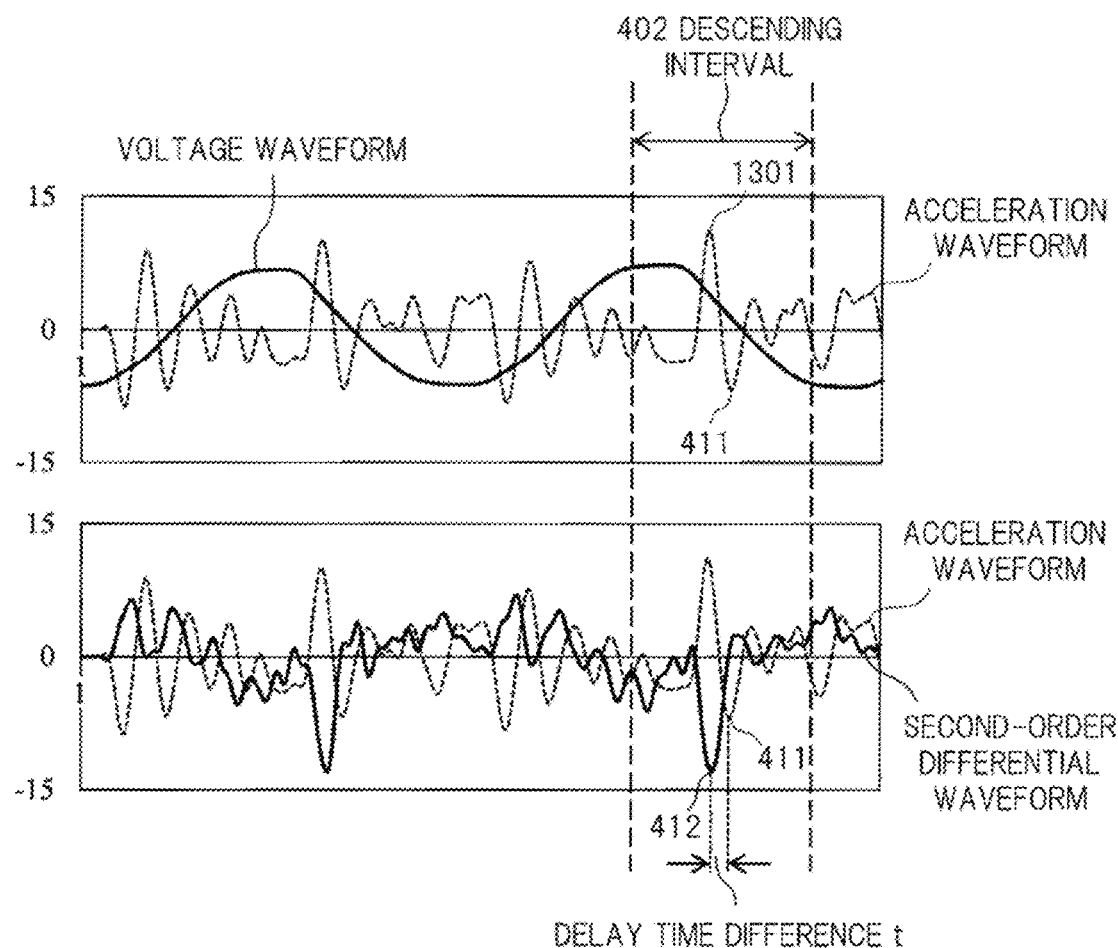
FIG. 13 is a diagram showing a delay time difference calculated by an acceleration waveform and a second-order differential waveform.

This calculation will be described with reference to FIG. 13. The waveform feature calculation unit 234 searches for the maximum value 1301 of the acceleration waveform in the descending interval 402 (from the period midpoint to the period end point), and records the position of the maximum value 1301. The waveform feature calculation unit 234 then searches for a first local minimum value from the position of the maximum value 1301, and records the position of the local minimum value. In this case, the local minimum value will be referred to as an acceleration maximum changing point 411.

At the same time, the waveform feature calculation unit 234 searches for the minimum value of the second-order differential waveform in the descending interval 402 (from the period midpoint to the period end point), and records the position of the minimum value. In this case, the minimum value will be referred to as a second-order differential maximum changing point 412.

The waveform feature calculation unit 234 then compares the position of the acceleration maximum changing point 411 with the position of the second-order differential maximum changing point 412, and estimates a time difference at the position to be a delay time difference t between the acceleration waveform and the second-order differential waveform in each interval. The waveform feature calculation unit 234 calculates the delay time difference t for each interval, and estimates the average value of the delay time differences T to be the delay time difference T (step S316). The waveform feature calculation unit 234 outputs the delay time difference T to the calculation unit 235.

Incidentally, although the method of calculating the delay time difference t in the descending interval 402 has been described with reference to FIG. 13, the delay time difference t can be calculated from the acceleration maximum changing point and the second-order differential maximum changing point also in the ascending interval similarly to the descending interval.

According to the third example, since the delay time difference is calculated for each interval of the period, the delay time difference can be calculated even in a small number of intervals. Therefore, the number of times of pressing the measurement apparatus 1 can be reduced, which makes it possible to shorten a measurement time.

A calculation in step S4 of FIG. 7 will be described next. The calculation unit 235 calculates a viscosity component(s) and an elasticity component(s) based on the complex elastic modulus K outputted from the conversion coefficient calculation unit 233 and a delay time difference T outputted from the waveform feature calculation unit 234 (step S4).

In this case, assume that a frequency at which the measurement apparatus is pressed against the object by the operator or a motor is set at fHz. A phase difference D is calculated from the delay time difference T by using the frequency fHz (equation (6)) (step S34).

[Math 4]

$$D = T \times f \times 360 \qquad \text{Equation (6)}$$

The calculation unit 235 then multiplies an absolute value K of a complex elastic modulus indicating dynamic viscoelasticity by the phase difference D to calculate a storage elastic modulus E' and a loss elastic modulus E" (equations (7) and (8)).

[Math 5]

$$E' = K \times \cos D \qquad \text{Equation (7)}$$

$$E'' = K \times \sin D \qquad \text{Equation (8)}$$

In this case, the storage elastic modulus E' is set as an elasticity component, and the loss elastic modulus E" is set as a viscosity component. Thereafter, in step S7, a display unit 26 may display a numerical value representing the storage elastic modulus E' as information on the elasticity component and a numerical value representing the loss elastic modulus E" as information on the viscosity component. Incidentally, as the delay time difference T increases, the viscosity component increases.

Figure 14A:
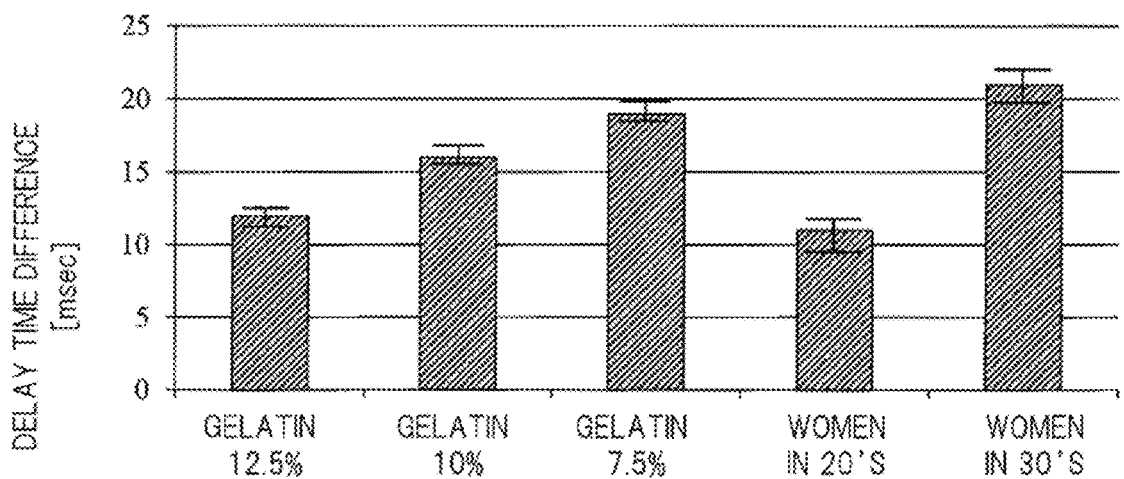
FIG. 14A is a diagram showing calculation results on delay time differences between gelatin and human skins.
Figure 14B:
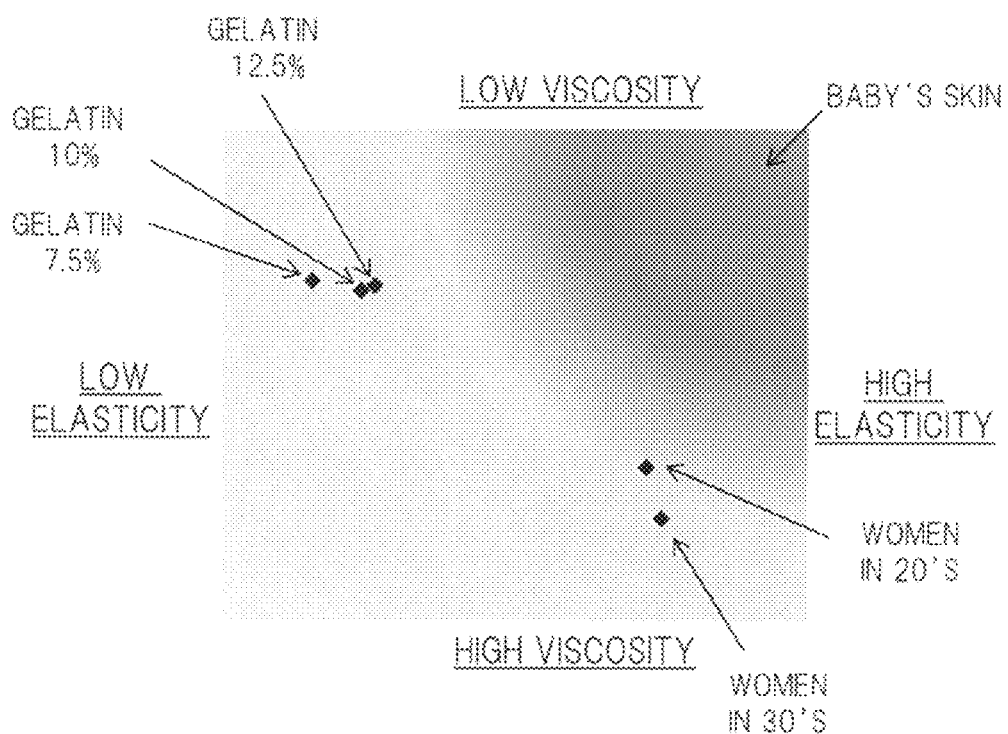
FIG. 14B is a distribution chart in which measurement results on elasticity components and viscosity components are shown on a graph representing a first axis of the elasticity component and a second axis of the viscosity component.

An example of a display in step S7 will be described next. First of all, collagen (gelatin powder), which is known as having a function of retaining skin elasticity and tenseness, is heated and decomposed together with water, and its mass is formed after cooling. In this case, a ratio between the gelatin power and water may be set to be almost equal to a proportion of collagen contained in the human skin, or may be set to a portion that allows gelatin to solidify. FIGS. 14A and 14B each show a result obtained by using the above mass and measuring elasticity and viscosity, and a result obtained by using the facial skins of women in their 20's and 30's and measuring elasticity and viscosity. FIG. 14A shows the result of delay time differences as information on the elasticity and the viscosity. FIG. 14B is a distribution chart in which a result of measured elasticity components and viscosity components are shown on a graph having first and second axes respectively representing an elasticity component and a viscosity component. Note that in these measurement experiments, only typical results have been extracted from many measurement results, and FIGS. 14A and 14B each show only some typical data.

As shown in FIG. 14A, in a case of gelatin, as a gelatin concentration increase, a delay time difference decreases. As the gelatin concentration increases, the viscosity decreases (that is, the gelatin quickly restores its original shape after application of a force), and the elasticity increases. On the other hand, the human skin exhibits a shorter delay time difference with a decrease in age. Therefore, younger women in age exhibit lower viscosity and higher elasticity. Referring to the measurement results in FIG. 14A makes it possible to know that a tendency of gelatin matches with a tendency of the human skin about the delay time difference.

Note that in actual measurements, the display unit 26 may display delay time differences in respective age categories as shown in FIG. 14A. In this case, in a one-time measurement, variations in phase shift calculated for each period are indicated by an error bar. The calculation unit 235 may calculate information on the elasticity component and the viscosity component by using the average or center value of calculated delay time differences. By this, the calculation is thought to have high accuracy even in an unstable measurement environment.

FIG. 14B is a distribution chart of results of the measured elasticity components and viscosity components. An upper right part of the chart of FIG. 14B assumes baby's skins. Referring to FIG. 14B, the elasticity of the human skin is higher than that of gelatin. This is because the elasticity of the human skin increases due to influences of muscles and bones under the skin. Like an example of FIG. 14B, in the display unit 26, the information on the elasticity component and the viscosity component of each measurement object person may be displayed on a two-dimensional plane having two exes corresponding to them.

Alternatively, the storage unit 24 may store a database representing a correlation between the viscosity and elasticity and a state(s) or category (categories) of the measurement objects. As one example, the database may include a relationship among human ages (or age categories) and a range of numerical values representing the viscosity components, and a relationship between human ages (or age categories) and a range of numerical values representing the elasticity components. The calculation unit 235 may cause the display unit 26 to display comparison results of measurement results and information stored in the database by referring to the database described above.

Figure 15:
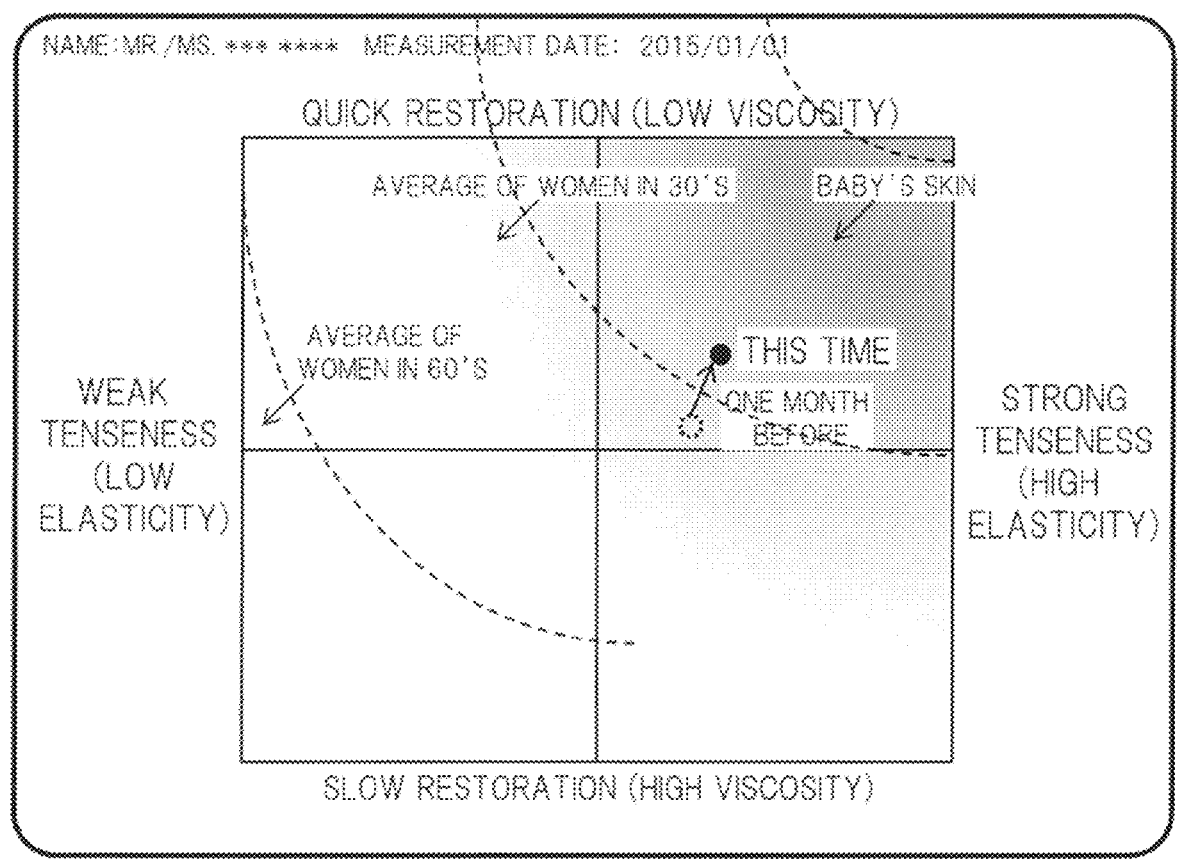
FIG. 15 is a first example of a display on a display unit.

FIG. 15 shows an example of a display on the display unit 26 using the database. In the display unit 26, information on the elasticity component and the viscosity component of each measurement object person is displayed on a two-dimensional plane having first and second axes respectively representing the elasticity component and the viscosity component. In addition, comparison object data in the database may be superimposedly displayed on the two-dimensional plane of the display unit 26. In the display unit 26, baby's skin data, average data about women in their 30's, and average data about women in their 60's are displayed as the comparison object data in the form of radial distribution data with an upper right point being set at the origin (broken lines in FIG. 15). In this manner, the comparison object data may be radially displayed on the two-dimensional plane from a given reference point. This makes it possible to easily comprehend which age category a combination of the elasticity and the viscosity of each measurement object person is close to. In addition, the storage unit 24 may further store a database recording a history of information on the elasticity component and information on the viscosity component of each measurement object person. A gross chart of the measurement results is superimposedly displayed on the display unit 26. In an example of FIG. 15, one month age measurement results and current measurement results of each measurement object person are displayed on the two-dimensional plane.

As another example, the calculation unit 235 may output a skin age or age category of each measurement object person (such as 20's and 30's) by using the elasticity component information and the viscosity component information calculated in step S4 and referring to the above database. The calculation unit 235 may output skin ages concerning each of the elasticity component and the viscosity component, or output skin ages from a combination of the elasticity component and the viscosity component. Therefore, the display unit 26 may display the skin ages or age categories corresponding to the elasticity component information and the viscosity component information obtained by the calculations.

As yet another example, the calculation unit 235 may cause the display unit 26 to display a radar chart of skin features by using the elasticity component information and the viscosity component information calculated in step S4 and referring to the above database. The radar chart is a radially displayed chart in which a plurality of items are each set as a longitudinal axis, and the origins of the longitudinal axes are brought together. In this case, the items of the radar chart may include elasticity components, viscosity components, and other items (such as skin's moisture amount). A piece of standard data concerning a given age (or age category) may be superimposedly displayed as a reference result of the database on the radar chart. Using the radar chart makes it possible to check an overall balance by connecting adjacent plots with a straight line.

Figure 16:
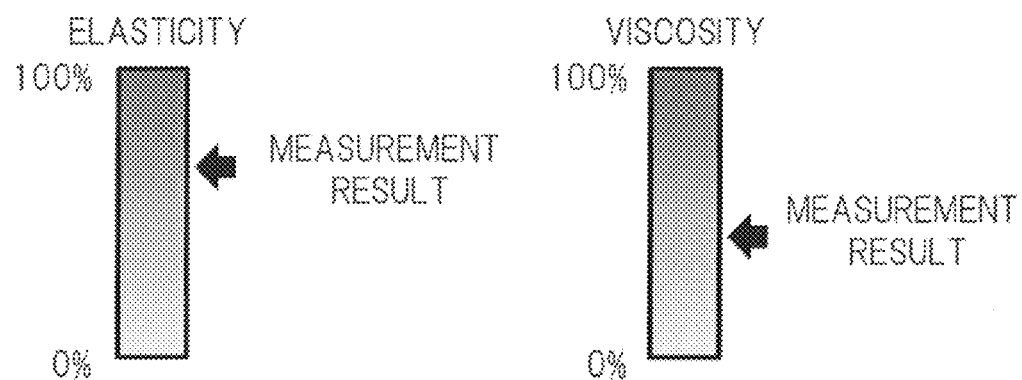
FIG. 16 is a second example of a display on the display unit.

The calculation unit 235 may form a chart for each classification by using the elasticity component information and the viscosity component information calculated in step S4 and referring to the above database. FIG. 16 shows an example of displaying elasticity component information and viscosity component information for each classification. Assume that in this case, the maximum and minimum values in numerical value information about each of elasticity and viscosity components are set to 100% and 0%, respectively. In the display unit 26, a position indicating a numerical value associated with each measurement object person is displayed concerning each of elasticity and viscosity.

Incidentally, although several chart examples have been illustrated above, the display unit 26 may display the numerical value information on each of the elasticity components and the viscosity components and at least one of the charts described above.

In addition, the viscoelasticity calculation system 1000 according to this embodiment calculates the voltage/displacement conversion coefficient $C_{md}$ by comparing the second-order differential waveform generated on the basis of the voltage information acquired from the magnetic sensor 19 with the acceleration waveform based on the acceleration information acquired from the acceleration sensor 13. The viscoelasticity calculation system 1000 then calculates the complex elastic modulus K of the object by dividing the previously obtained voltage/pressure conversion coefficient $C_{mp}$ by the voltage/displacement conversion coefficient $C_{md}$. In addition, the viscoelasticity calculation system 1000 also calculates an elasticity component(s) and a viscosity component(s) from the complex elastic modulus K and the delay time difference T. This makes it possible to calculate, with high accuracy, dynamic viscoelasticity indicating a viscoelasticity feature(s) of the object regardless of a feature of a dent of the object in its pressing time. Using the acceleration sensor 13 and the magnetic sensor 19, in particular, makes it possible to easily achieve reductions in size and cost of the measurement apparatus 1.

In addition, the viscoelasticity calculation system 1000 of the present embodiment can perform highly accurate measurement by using the acceleration sensor 13 for dynamic measurement. Furthermore, the viscoelasticity calculation system 1000 according to the embodiment can quantitatively calculate the dynamic viscoelasticity even about the object to which a measurement apparatus is difficult to be fixed at a measurement time. When measuring the human body, in particular, the viscoelasticity calculation system 1000 can perform highly accurate measurement even at a region that is difficult to maintain its initial position in.

Incidentally, as a means for acquiring a voltage waveform for measurement of reactive force information, a displacement sensor, stress sensor, acceleration sensor, or the like may be used in place of the magnetic sensor.

Second Embodiment

Figure 19:
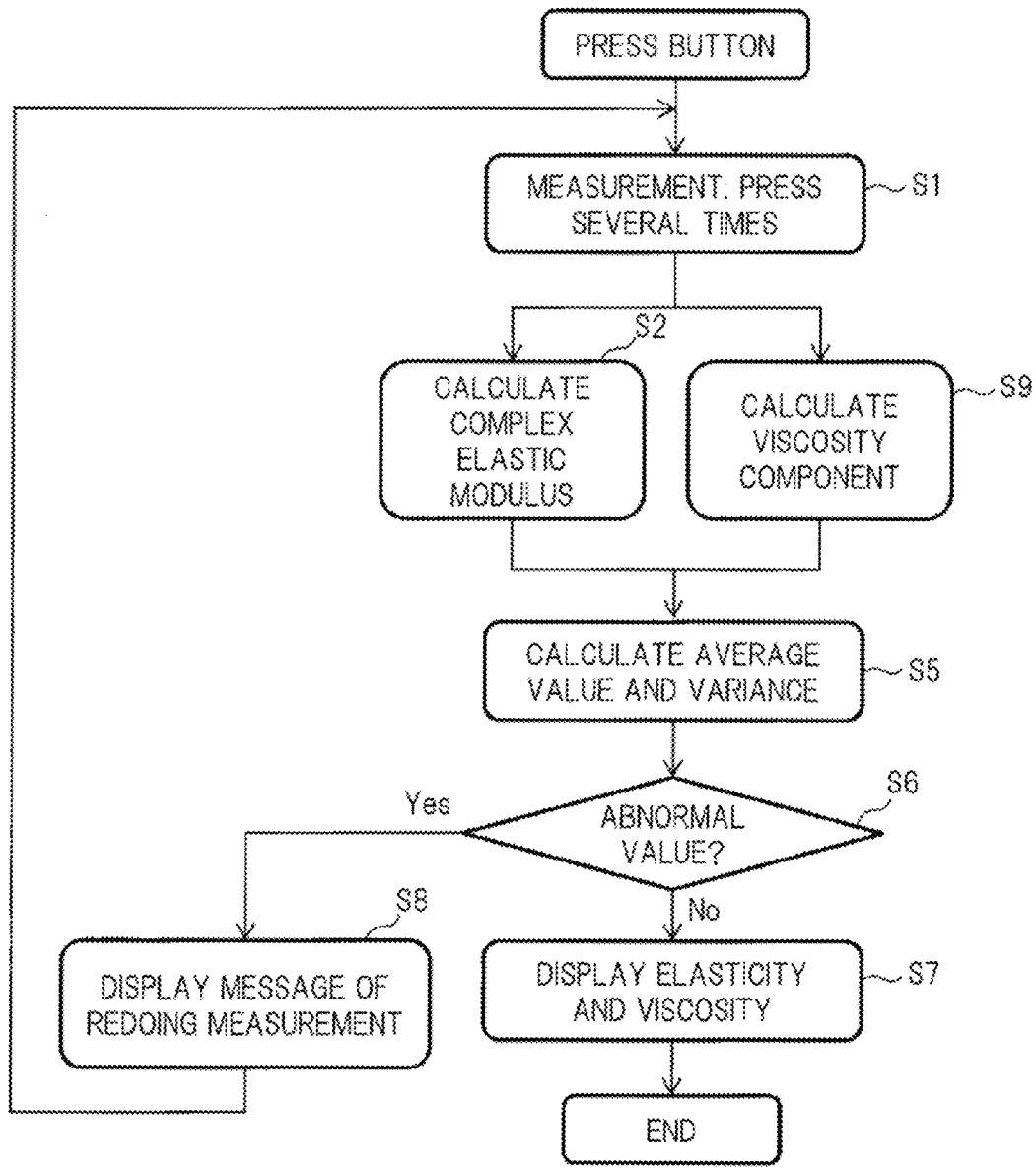
FIG. 19 is an example of a flowchart showing a flow of the overall processings in a viscoelasticity calculation system (second embodiment)

FIG. 19 is a flowchart for explaining processings by a viscoelasticity calculation system 1000 according to a second embodiment. Note that the same step numbers denote the same steps as those in FIG. 7, and a description of them will be omitted.

There is a possibility that viscosity components and elasticity components will be difficult to quantify due to noise and the like. In this embodiment, step S9 that allows qualitative calculation of a viscosity component(s) is executed in place of step S3 in FIG. 7. Note that in this embodiment, the complex elastic modulus calculated in step S2 is regarded as information on an elasticity component, and a value calculated in step S9 is regarded as information on a viscosity component. A calculation processing example in step S9 will be described.

First Example

Example of Using Acceleration Waveform and Voltage Waveform

Figure 20:
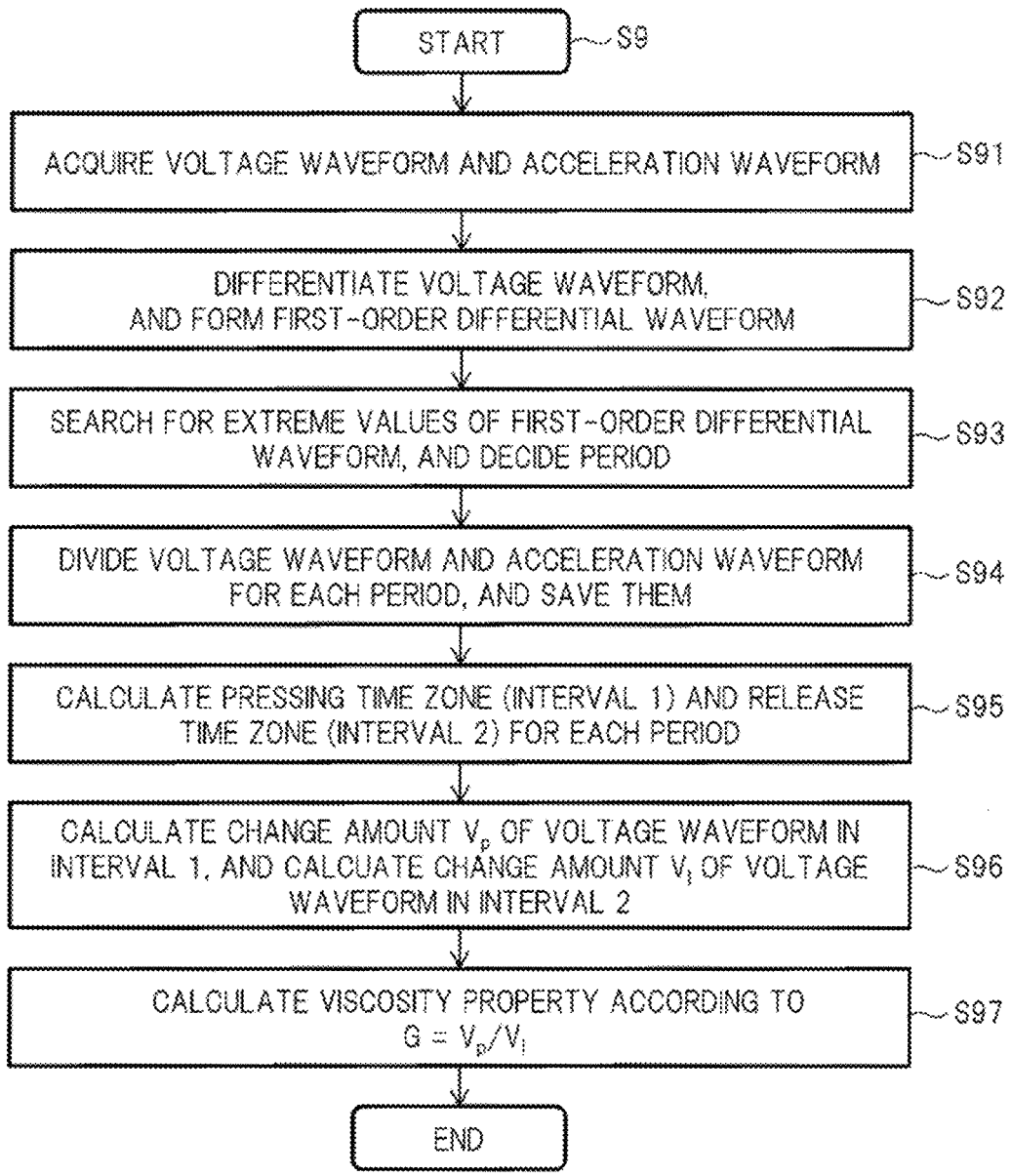
FIG. 20 is a flowchart showing a first example of step S9 of FIG. 19.

FIG. 20 shows a first example of a flowchart in step S9. A microprocessor 23 acquires a voltage waveform based on information on a voltage acquired from the magnetic sensor 19 via the driving circuit 21, and an acceleration waveform based on information on the acceleration acquired from the acceleration sensor 13 via the driving circuit 22 (step S91). The voltage waveform is inputted to the differential waveform generation unit 231. The acceleration waveform is inputted to the waveform feature calculation unit 234. In FIG. 12, (a) shows the acceleration waveform. In FIG. 12, (b) shows the voltage waveform.

The differential waveform generation unit 231 then generates a first-order differential waveform from the voltage waveform (step S92). The differential waveform generation unit 231 outputs the first-order differential waveform to the waveform feature calculation unit 234. In FIG. 12, (c) shows the first-order differential waveform of the voltage waveform.

The waveform feature calculation unit 234 searches for extreme values of the first-order differential waveform and decides a period (step S93). A period decision method will be described in detail below. First of all, the waveform feature calculation unit 234 calculates an average value of the first-order differential waveform. The waveform feature calculation unit 234 then calculates the average value of the first-order differential waveform, calculates an amplitude k of the first-order differential waveform, and calculates a value of 0.3 times the amplitude k.

The waveform feature calculation unit 234 then searches for data smaller than (average−amplitude k×0.3) from on the first-order differential waveform, and saves the searched continuous data as one interval. In FIG. 12, a broken line 1201 in (c) represents an interval smaller than (average value−amplitude k×0.3). The waveform feature calculation unit 234 obtains the minimum value of each interval 1201, and saves a position of the minimum value as a period dividing point of the first-order differential waveform. In FIG. 12, a point 1202 in (c) indicates the minimum value of a given interval 1201.

The waveform feature calculation unit 234 then searches for data larger than (average+amplitude k×0.3) from on the first-order differential waveform, and saves the searched continuous data as one interval. In FIG. 12, a broken line 1203 in (c) indicates an interval larger than (average value+amplitude k×0.3). The waveform feature calculation unit 234 obtains the maximum value 1204 of each interval 1203, and saves a position of the maximum value 1204 as a period midpoint of the voltage waveform. Therefore, a period of the voltage waveform can be defined by an ascending interval 401 and a descending interval 402 between two period dividing points (minimum values 1202).

The waveform feature calculation unit 234 then divides the acceleration waveform and the voltage waveform for each period in accordance with period dividing points, and saves the divided waveforms (step S94). As described above, with regard to the voltage waveform, an interval from a period start point to a period midpoint is called the ascending interval 401, and an interval from the period midpoint to a period end point is called the descending interval 402.

The waveform feature calculation unit 234 then calculates a pressing time zone and a release time zone for each period (step S95). The waveform feature calculation unit 234 obtains a pressing time zone and a release time zone on the basis of continuous local maximum and local minimum values in the intervals 401 and 402. Incidentally, since the same calculation is performed in each period, the calculation in one period will be described below with reference to FIG. 21 in this case.

The waveform feature calculation unit 234 searches for the minimum value of the acceleration waveform in a range of the ascending interval 401, and records a position of the minimum value. The waveform feature calculation unit 234 then searches for a first local maximum value from the position of the minimum value, and records a position of the maximum value. An interval between the recorded minimum and maximum values is called a pressing time zone 421.

The waveform feature calculation unit 234 searches for the maximum value of the acceleration waveform in a range of the descending interval 402, and records a position of the maximum value. The waveform feature calculation unit 234 then searches for the first local minimum value from the position of the maximum value, and records a position of the minimum value. An interval between the recorded maximum and minimum values is called a release time zone 422.

The waveform feature calculation unit 234 then calculates a change amount Vp of the voltage waveform in the specified pressing time zone 421, and calculates a voltage change amount Vl in the specified release time zone 422 (step S96). The waveform feature calculation unit 234 outputs the change amounts Vp and Vl to the calculation unit 235.

The calculation unit 235 then calculates a viscosity property G according to equation (9) (step S97).

[Math 6]

$$G = \frac{V_p}{V_i}$$ Equation (9)

Figures 21, 22:
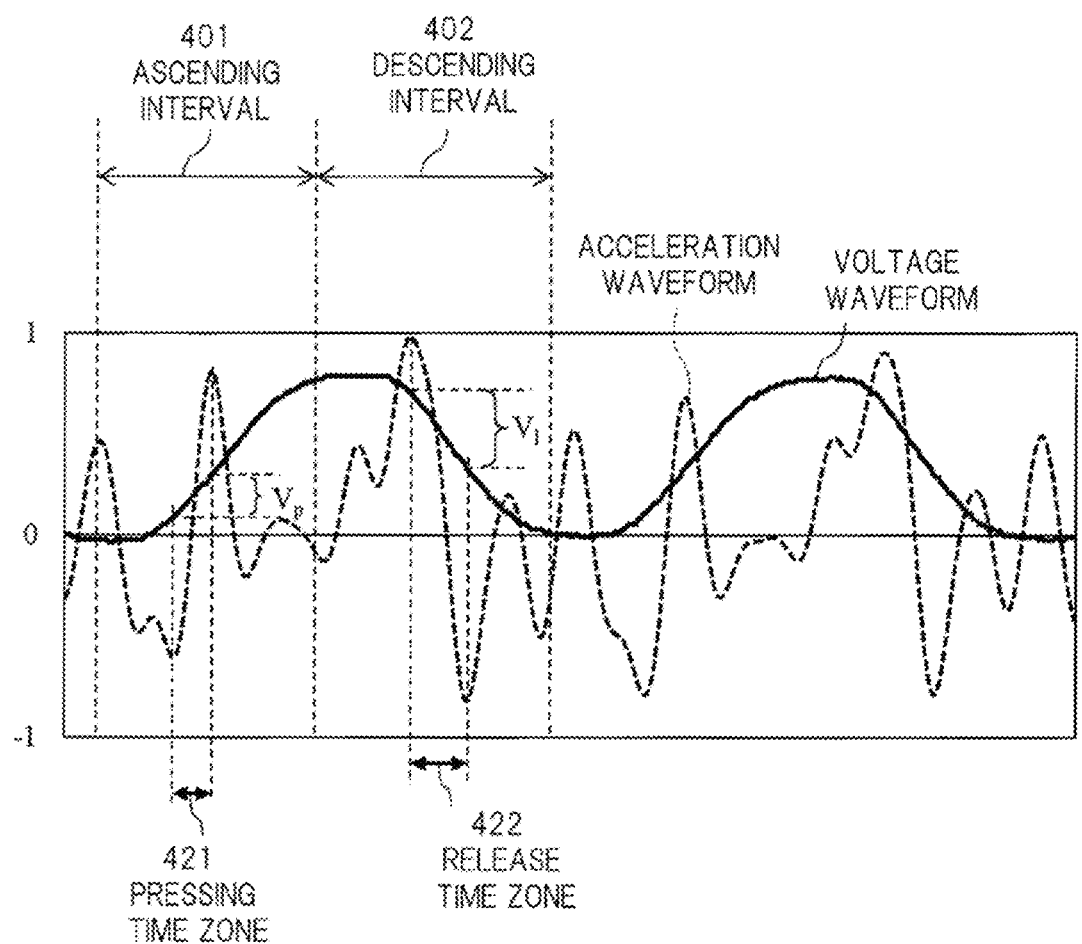
FIG. 21 is a diagram showing a calculation processing of a viscosity component due to acceleration waveform and a voltage waveform.
FIG. 22 is a diagram showing calculation results on human-skin viscosity components.

Here, the viscosity property G will be described below. When the measurement apparatus 1 is pressed, higher viscosity generates a larger reactive force due to the viscosity property. When the measurement apparatus 1 is released, higher viscosity generates a smaller reactive force due to the viscosity property. Vp and Vl represent measurement values based on a comprehensive effect of the viscosity property and the elasticity property. The viscosity property G, which is a ratio between Vp and Vl, qualitatively indicates a degree of contribution of viscosity to the viscoelasticity properties. As the viscosity property G increases, the viscosity component increases. FIG. 21 shows measurement results of the viscosity property G obtained at two places on a facial skin of each of persons in their 20's and 30's. As shown in FIG. 21, the value of the viscosity property G increases as the measurement object person gets older. It is understood also from the results shown in FIG. 21 that the viscosity property G as the ratio between Vp and Vl is useful as a numerical value indicating a degree of the viscosity in the viscoelasticity properties.

Note that an average value, a median, or the like of values calculated in a plurality of intervals may be used as the change amounts Vp and Vl.

Incidentally, the calculation unit 235 may cause a display unit 26 to display the viscosity property G as viscosity component information in step S7. The calculation unit 235 may also cause the display unit 26 to display complex elastic modulus information as elasticity component information. In addition, similarly to the first embodiment, various types of charts may be displayed on the display unit 26 by using a database representing a correlation between human age and the viscosity property G.

When a second-order differential waveform generated on the basis of a voltage waveform becomes complex due to a noise(s) and the like, a delay(s) sometimes occurs in forming the second-order differential waveform. In this case, there is a possibility that a phase difference between the second-order differential waveform and the voltage waveform cannot be properly extracted. According to the first example, even in the presence of much noise or the like, the viscosity property G useful as a qualitative evaluation of a viscosity feature can be estimated.

Second Example

Example of Using Only Acceleration Waveform

Figure 23:
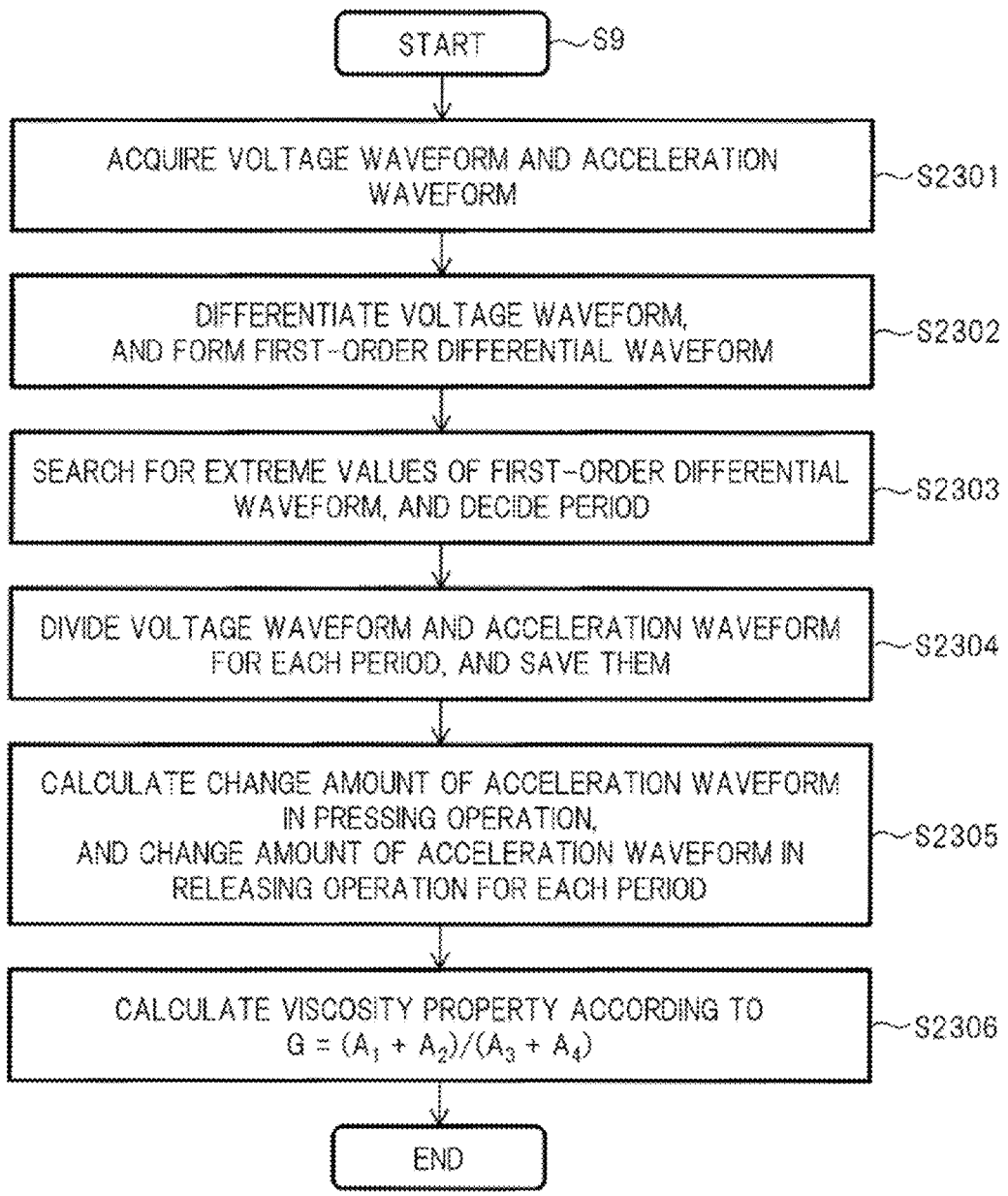
FIG. 23 is a flowchart showing a second example of step S9 of FIG. 19.

FIG. 23 shows a second example of a flowchart in step S9. Note that processings in steps S2301 to S2304 are the same as those in steps S91 to S94 in FIG. 20, and hence a description of them will be omitted.

Figure 24:
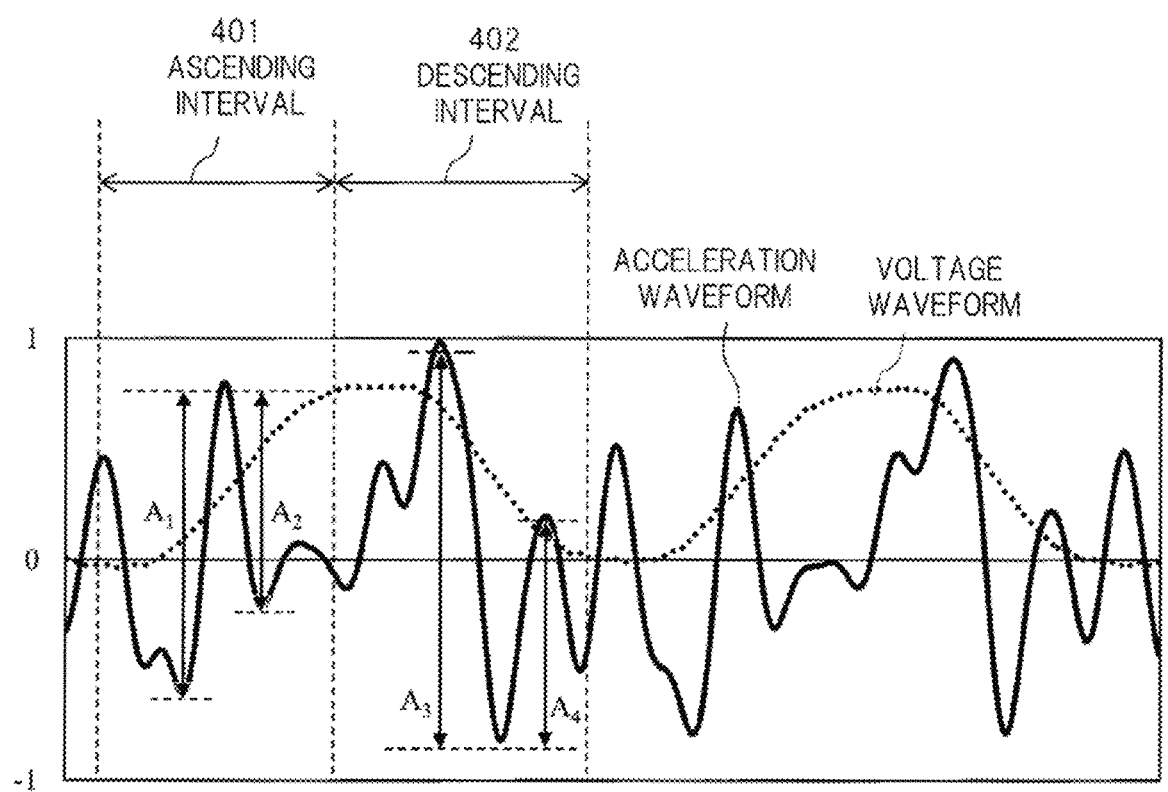
FIG. 24 is a diagram showing a calculation processing of a viscosity component due to an acceleration waveform and a voltage waveform.

After step S2304, the waveform feature calculation unit 234 calculates a change amount of the acceleration waveform of the measurement apparatus 1 in the pressing time zone, and a change amount of the acceleration waveform of the measurement apparatus 1 in the release time zone (step S2305). The pressing time zone and the release time zone are obtained by continuous local maximum and local minimum values in the intervals 401 and 402. Incidentally, since the same calculation is performed for each period, the calculation in one period will be described below with reference to FIG. 24 in this case.

The waveform feature calculation unit 234 searches for the minimum value of the acceleration waveform in the range of the ascending interval 401, and records its position as the first minimum value. The waveform feature calculation unit 234 searches for a first local maximum value from the position of the first minimum value, and records its position as the first maximum value. The waveform feature calculation unit 234 then searches for a next local minimum value from the position of the first maximum value, and records the position of the local minimum value as the second minimum value. Thereafter, the waveform feature calculation unit 234 calculates a change amount A1 of the acceleration waveform between the first minimum value and the first maximum value, and a change amount A2 of the acceleration waveform between the first maximum value and the second minimum value. The waveform feature calculation unit 234 then outputs, to the calculation unit 235, a total change amount A1+A2 in the ascending interval 401.

Subsequently, the waveform feature calculation unit 234 searches for the maximum value of the acceleration waveform in the range of the descending interval 402, and records its position as the first maximum value. The waveform feature calculation unit 234 then searches for a first local minimum value from the position of the first maximum value, and records its position as the first minimum value. The waveform feature calculation unit 234 then searches for a next local maximum value from the position of the first minimum value, and records a position of the local maximum value as the second maximum value. Thereafter, the waveform feature calculation unit 234 calculates a change amount A3 of the accelerations between the first maximum value and the first minimum value, and a change amount A4 of the accelerations between the first minimum value and the second maximum value. The waveform feature calculation unit 234 also outputs, to the calculation unit 235, a total change amount A3+A4 in the descending interval 402.

The calculation unit 235 then calculates the viscosity property G according to equation (10) (step S2306).

[Math 7]

$$G = \frac{A_1 + A_2}{A_3 + A_4}$$ Equation (10)

Here, the viscosity property G will be described below. When the measurement apparatus 1 is pressed, higher viscosity generates a larger reactive force due to the viscosity property. When the measurement apparatus 1 is released, higher viscosity generates a smaller reactive force due to the viscosity property. A1+A2 and A3+A4 of the acceleration waveform reflect reactive force features concerning pressing and releasing operations, respectively. The viscosity property G as a ratio between A1+A2 and A3+A4 qualitatively indicates a degree of contribution of viscosity to the viscoelasticity property. As a value of G increases, a quantity of viscosity components increases.

Note that an average value, a median, or the like of the values calculated in a plurality of intervals may be used as the change amounts A1, A2, A3, and A4.

Incidentally, the calculation unit 235 may cause the display unit 26 to display the viscosity property G as viscosity component information in step S7. The calculation unit 235 may also cause the display unit 26 to display complex elastic modulus information as elasticity component information. In addition, similarly to the first embodiment, various types of charts may be displayed on the display unit 26 by using a database representing a correlation between human age and the viscosity property G.

According to the second example, information on the viscosity components can be calculated only by the acceleration waveform. Note that discrimination between the ascending interval and the descending interval by providing a switch for the measurement apparatus 1 may be made as a method of obtaining the viscosity property G besides use of the voltage waveform.

Third Example

Example of Using Only Voltage Waveform

Figure 25:
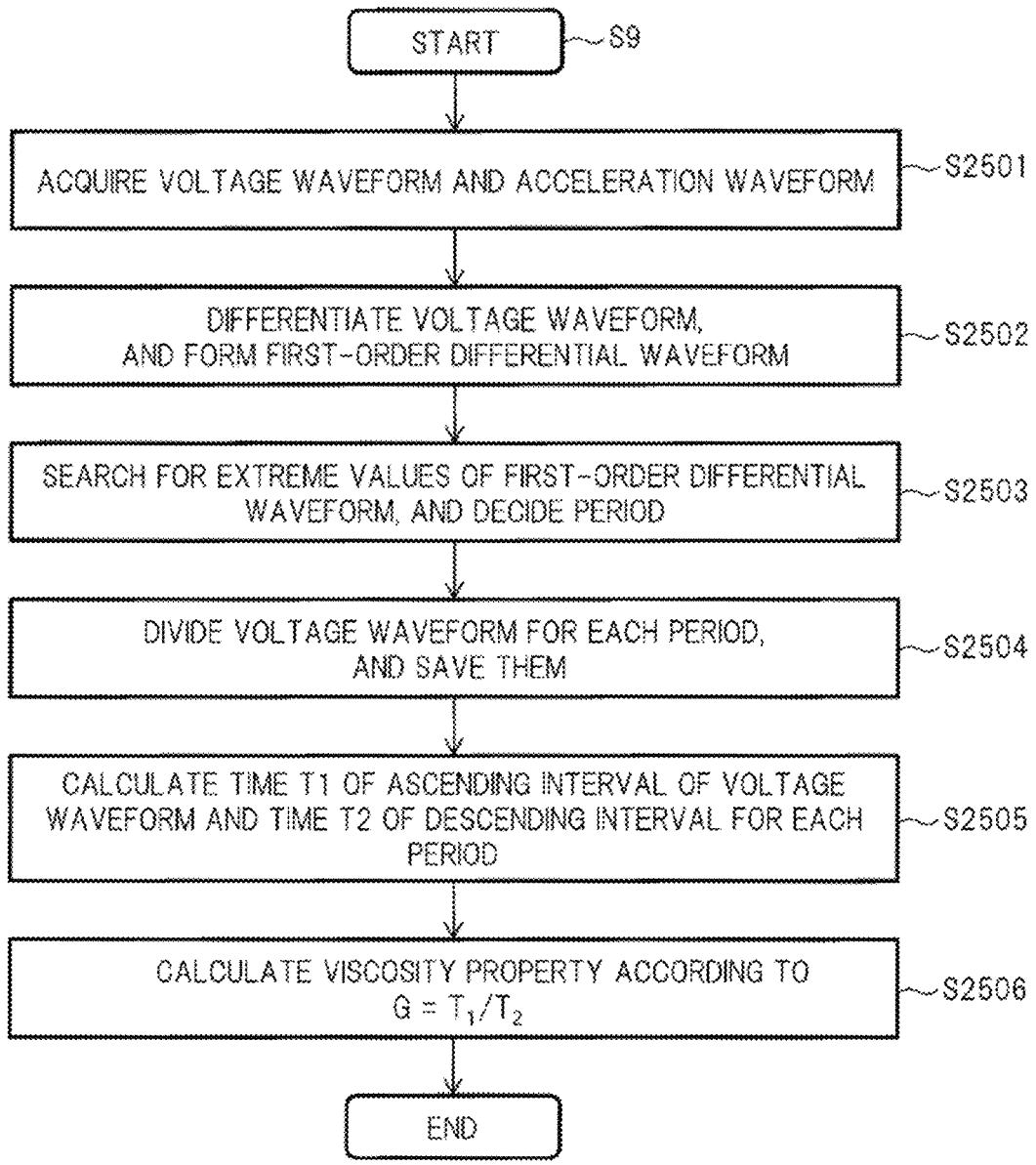
FIG. 25 is a flowchart showing a third example of step S9 in FIG. 19.

FIG. 25 shows a third example of a flowchart in step S9. Note that processings in steps S2501 to S2503 are the same as those in steps S91 to S94 in FIG. 20, and hence a description of them will be omitted.

After step S2503, the waveform feature calculation unit 234 divides a voltage waveform according to period dividing points and saves the divided waveforms (step S2504). With regard to the voltage waveform as described above, an interval from a period start point to a period midpoint is called the ascending interval 401, and an interval from the period midpoint to a period end point is called the descending interval 402.

The waveform feature calculation unit 234 then calculates a time T1 of the ascending interval 401 of the voltage waveform and a time T2 of the descending interval 402 of the voltage waveform for each period (step S2505). The waveform feature calculation unit 234 outputs the time T1 of the ascending interval 401 and the time T2 of the descending interval 402 to the calculation unit 235. FIG. 26 shows a calculation example of the times T1 and T2. Incidentally, since the same calculation is performed for each period, the calculation in one period will be described below.

The calculation unit 235 calculates the viscosity property G according to equation (11) (step S2506).

[Math 8]

$$G = \frac{T_1}{T_2} \qquad \text{Equation (11)}$$

Here, the viscosity property G will be described below. It can be considered that higher viscosity will cause a significantly larger delay due to the viscosity property in releasing the measurement apparatus 1. The viscosity property G as a ratio between the time T1 of the ascending interval 401 and the time T2 of the descending interval 402 qualitatively indicates a degree of contribution of the viscosity to the viscoelasticity properties. As the viscosity is higher, smaller becomes a reduce the ratio between the time T1 of the ascending interval 401 corresponding to the pressing time zone of the measurement apparatus 1 and the time T2 of the descending interval 402 corresponding to the release time zone of the measurement apparatus 1.

Note that an average value, a median, or the like of values calculated in a plurality of intervals may be used as the time T1 of the ascending interval 401 and the time T2 of the descending interval 402.

Incidentally, the calculation unit 235 may cause the display unit 26 to display the viscosity property G as viscosity component information in step S7. The calculation unit 235 may also cause the display unit 26 to display complex elastic modulus information as elasticity component information. In addition, similarly to the first embodiment, various types of charts may be displayed on the display unit 26 by using a database representing a correlation between human age and the viscosity property G.

According to the third example, information on the viscosity components can be calculated by using only the voltage waveform.

The present invention is not limited to the embodiments described above and includes various modification examples. The embodiments above have been described in detail so as to make the present invention easily understood, and the present invention is not always limited to the embodiment having all of the described constituent elements. Also, a part of the configuration of one embodiment may be replaced with the configuration of another embodiment, and the configuration of one embodiment may be added to the configuration of another embodiment. Furthermore, another configuration may be added to a part of the configuration of each embodiment, and a part of the configuration of each embodiment may be eliminated or replaced with another configuration.

Various types of processing performed by the microprocessor 23 described above can also be realized by program codes of software for implementing their functions. In this case, a storage medium recording the program codes is provided to a system or apparatus, and a computer (or CPU or MPU) in the system or apparatus reads out program codes stored in the storage medium. In this case, the program codes themselves read out from the storage medium realize the functions of the embodiments described above, and hence the program codes themselves and the storage medium recording them constitute the present invention. As storage media for supplying such program codes, a flexible disk, CD-ROM, DVD-ROM, hard disk, optical disk, magneto-optical disk, CD-R, magnetic tape, nonvolatile memory card, ROM, and the like are used.

The processes and techniques described herein are not essentially associated with any specific apparatuses, and can be implemented even by any combinations commensurate with components. In addition, various general-purpose types of devices can be used. Constructing a dedicated apparatus is sometimes useful to perform the steps in the methods described herein. That is, some or all of the processings performed by the microprocessor 23 described above may be realized by hardware using electronic components such as integrated circuits.

Furthermore, in the above embodiments, control lines and information lines considered necessary for explanations are illustrated, but do not necessary illustrate all the control lines and information lines in terms of products. All the arrangements may be connected to each other.

REFERENCE SIGNS LIST

1000 . . . viscoelasticity calculation system
1, 1a . . . measurement apparatus
2 . . . viscoelasticity calculation apparatus
11 . . . receiving coil 12 . . . transmitting coil
13 . . . acceleration sensor (first sensor)
14 . . . main body unit
15 . . . movable unit
16, 16a . . . spring
17(a) . . . spring
17(b) . . . dashpot
18 . . . battery
19 . . . magnetic sensor (second sensor)
20 . . . contact portion
21, 22 . . . driving circuit
23 . . . microprocessor
24 . . . storage unit
25 . . . sound generation unit
26 . . . display unit
27 . . . power source unit
28 . . . input unit
31 . . . AC oscillation source
32 . . . amplifier
33 . . . preamplifier
34 . . . detection circuit
35 . . . reference signal
36 . . . low-pass filter
110 . . . coil board
120 . . . coil board
130 . . . operating circuit board
190 . . . operation button
231 . . . differential waveform generation unit
232 . . . waveform comparison unit
233 . . . conversion coefficient calculation unit
234 . . . waveform feature calculation unit
235 . . . calculation unit
236 . . . determination unit
801, 802 . . . FFT unit
803, 804 . . . whitening unit
805 . . . multiplying unit
806 . . . IFFT unit
807 . . . maximum peak detection unit

The invention claimed is:

1. A viscoelasticity measurement system comprising:
a measurement apparatus including a movable unit configured to be continuously pressed against a measurement object, a first sensor configured to output acceleration information corresponding to an acceleration of pressing-directional movement of a contact portion of the movable unit with respect to the measurement object, and a second sensor configured to output reactive force information corresponding to a reactive force applied to the contact portion of the movable unit with respect to the measurement object;
a processor configured to calculate, based on the acceleration information and the reactive force information, a complex elastic modulus of the measurement object, a delay time difference between the acceleration information and the reactive force information, and a viscosity property, and calculate first information on an elastic component of the measurement object and second information on a viscosity component of the measurement object;
a display apparatus configured to display the first information and the second information.

2. The viscoelasticity measurement system according to claim 1,
wherein the processor is configured to calculate a complex elastic modulus of the measurement object by using an acceleration waveform acquired as the acceleration information and a second-order differential waveform of a voltage waveform acquired as the reactive force information,
the processor is configured to calculate, as the delay time difference, a phase difference between the acceleration waveform and the second-order differential waveform by using the acceleration waveform and the second-order differential waveform, and
the processor is configured to calculate the first information and the second information by using the complex elastic modulus and the phase difference.

3. The viscoelasticity measurement system according to claim 2,
wherein the processor is configured to calculate a time difference between the acceleration waveform and the second-order differential waveform based on a cross-correlation function of the acceleration waveform and the second-order differential waveform, and
the processor is configured to convert the time difference into the phase difference by using a frequency at which the movable unit is pressed against the measurement object.

4. The viscoelasticity measurement system according to claim 2,
wherein the processor is configured to calculate a time difference between the acceleration waveform and the second-order differential waveform based on a cross-power spectrum phase function between the acceleration waveform and the second-order differential waveform, and
the processor is configured to convert the time difference into the phase difference by using a frequency which is obtained from the acceleration information and the reactive force information and at which the movable unit is pressed against the measurement object.

5. The viscoelasticity measurement system according to claim 2,
wherein the processor is configured to calculate a delay time difference between a maximum changing point of the second-order differential waveform and a maximum changing point of the acceleration waveform, and
the processor is configured to convert the time difference into the phase difference by using a frequency which is obtained from the acceleration information and the reactive force information and the reactive force information and at which the movable unit is pressed against the measurement object.

6. The viscoelasticity measurement system according to claim 5,
wherein the processor is configured to divide the second-order differential waveform and the acceleration waveform into a plurality of intervals by using a first-order differential waveform of the voltage waveform, and
the processor is configured to calculate the maximum changing point of the second-order differential waveform and the maximum changing point of the acceleration waveform for each of the plurality of intervals.

7. The viscoelasticity measurement system according to claim 2,
wherein the processor is configured to calculate a voltage/displacement conversion coefficient indicating a ratio of a magnitude of the acceleration waveform to a magnitude of the second-order differential waveform, and
the processor is configured to calculate the complex elastic modulus by dividing, by the voltage/displacement conversion coefficient, a voltage/pressure conversion coefficient to be previously obtained.

8. The viscoelasticity measurement system according to claim 1,
   wherein the processor is configured to divide an acceleration waveform acquired as the acceleration information into a plurality of intervals by using a first-order differential waveform of a voltage waveform acquired as the reactive force information,
   the processor is configured to obtain a first time zone corresponding to pressing of the measurement apparatus and a second time zone corresponding to releasing of the measurement apparatus in the plurality of intervals of the acceleration waveform, and
   the processor is configured to calculate the viscosity property from a ratio between a change amount of the voltage waveform in the first time zone and a change amount of the voltage waveform in the second time zone, and calculates the viscosity as the second information.

9. The viscoelasticity measurement system according to claim 1,
   wherein the processor is configured to divide an acceleration waveform acquired as the acceleration information into a plurality of intervals by using a first-order differential waveform of a voltage waveform acquired as the reactive force information,
   the processor is configured to obtain a first time zone corresponding to pressing of the measurement apparatus and a second time zone corresponding to releasing of the measurement apparatus in the plurality of intervals of the acceleration waveform, and
   the processor is configured to calculate the viscosity property from a ratio between a change amount of the acceleration waveform in the first time zone and a change amount of the acceleration waveform in the second time zone, and calculates the viscosity property as the second information.

10. The viscoelasticity measurement system according to claim 1,
    wherein the processor is configured to obtain an ascending interval and a descending interval of the voltage waveform by using a first-order differential waveform of a voltage waveform acquired as the reactive force information, and
    the processor is configured to calculate the viscosity property from a ratio between a time of the ascending interval and a time of the descending interval, and calculates the viscosity property as the second information.

11. The viscoelasticity measurement system according to claim 1,
    wherein the display apparatus configured to display the first information and the second information on a two-dimensional plane having two axes respectively representing the elasticity component and the viscosity component.

12. The viscoelasticity measurement system according to claim 1, further comprising a storage unit including a first database that is configured to associate the first information and the second information with a state or category of the measurement object, corresponding to the first information and the second information by using the first database.

13. The viscoelasticity measurement system according to claim 1, further comprising a storage unit including a first database that is configured to associate the first information and the second information with a state or category of the measurement object,
    wherein the processor is configured to cause the display apparatus to display the first information and the second information on a two-dimensional plane having two axes respectively representing the elasticity component and the viscosity component and to superimposedly display comparison object data in the first database on the two-dimensional plane.

14. The viscoelasticity measurement system according to claim 13,
    wherein the comparison object data is displayed radially from a given reference point on the two-dimensional plane.

15. The viscoelasticity measurement system according to claim 1, further comprising a storage unit including a second database configured to record a history of the first information and the second information on the measurement object,
    wherein the processor is configured to cause the display apparatus to display the history of the first information and the second information on the measurement object by using the second database.

16. A viscoelasticity measurement method comprising the steps of:
    continuously pressing a movable unit of a measurement apparatus against a measurement object;
    causing a first sensor of the measurement apparatus to output acceleration information corresponding to an acceleration of pressing-directional movement of a contact portion of the movable unit with respect to the measurement object;
    causing a second sensor of the measurement apparatus to output reactive force information corresponding to a reactive force applied to the contact portion of the movable unit with respect to the measurement object;
    causing a processor to calculate based on the acceleration information and the reactive force information, a complex elastic modulus of the measurement object, a delay time difference between the acceleration information and the reactive force information and a viscosity property, and to calculate first information on an elasticity component of the measurement object and second information on a viscosity component of the measurement object; and
    displaying the first information and the second information on a display apparatus.

* * * * *